(12) United States Patent
Hegazi

(10) Patent No.: US 8,263,000 B2
(45) Date of Patent: Sep. 11, 2012

(54) APPARATUS AND METHOD FOR MEASURING CONCENTRATIONS OF FUEL MIXTURES USING DEPTH-RESOLVED LASER-INDUCED FLUORESCENCE

(75) Inventor: Ezzat M. Hegazi, Windsor (CA)

(73) Assignee: King Fahd University of Petroleum & Minerals, Dhahran (SA)

( * ) Notice: Subject to any disclaimer, the term of this patent is extended or adjusted under 35 U.S.C. 154(b) by 92 days.

(21) Appl. No.: 12/461,082

(22) Filed: Jul. 30, 2009

(65) Prior Publication Data

US 2009/0290152 A1    Nov. 26, 2009

Related U.S. Application Data

(62) Division of application No. 11/392,814, filed on Mar. 30, 2006, now Pat. No. 7,846,390.

(51) Int. Cl.
*G01N 21/00* (2006.01)
*G01N 21/64* (2006.01)
*G01N 21/62* (2006.01)
*G01J 3/18* (2006.01)
*G01J 3/40* (2006.01)

(52) U.S. Cl. ............... 422/82.05; 422/82.06; 422/82.07; 422/82.08; 356/300; 356/305; 356/318; 356/326; 356/329; 356/331; 250/458.1; 250/461.1

(58) Field of Classification Search ................. None
See application file for complete search history.

(56) References Cited

U.S. PATENT DOCUMENTS

| 3,947,124 A * | 3/1976 | West | 356/300 |
|---|---|---|---|
| 4,087,685 A | 5/1978 | Froot | 250/302 |
| 4,188,120 A | 2/1980 | McDonald | |
| 4,350,661 A | 9/1982 | Davis | |
| 4,365,153 A | 12/1982 | Seigel et al. | 250/253 |
| 4,759,033 A | 7/1988 | Ariessohn | |

(Continued)

FOREIGN PATENT DOCUMENTS

JP    6317512    11/1994

(Continued)

OTHER PUBLICATIONS

Patra, D. and Mishra, A.K., "Effect of sample geometry on synchronous fluorimetric analysis of petrol, diesel, kerosene and their mixtures at higher concentration," *Analyst*, vol. 125 (2000), pp. 1383-1386.

(Continued)

*Primary Examiner* — Neil N Turk
(74) *Attorney, Agent, or Firm* — Richard C. Litman

(57) ABSTRACT

The apparatus for measuring concentrations of fuel mixtures using depth-resolved laser-induced fluorescence is a fluorometer equipped with a sample container holder that is movable in the path of the beam from the light source. Fluorescent emissions from the sample mixture pass at 90° to the excitation light path through a slit that is narrow enough that the emission intensity is effectively produced by a thin layer of the sample and focused on a monochromator, with successive thin layers receiving nonuniform excitation radiation due to reduction of intensity along the excitation light source path with increasing depth penetration and due to reabsorption of emitted fluorescence from adjacent layers. The method has a first mode in which the emission spectrum is scanned at a fixed depth, and a second mode in which the sample is moved relative to the emission monochromator slit to vary the depth while keeping the emission wavelength fixed.

3 Claims, 28 Drawing Sheets

U.S. PATENT DOCUMENTS

| | | | |
|---|---|---|---|
| 4,877,966 A | 10/1989 | Tomei | |
| 5,049,738 A | 9/1991 | Gergely | |
| 5,198,871 A | 3/1993 | Hill, Jr. | |
| 5,424,841 A | 6/1995 | Van Gelder et al. | 356/417 |
| 5,656,810 A | 8/1997 | Alfano | |
| 5,859,704 A | 1/1999 | Fric | |
| 6,124,597 A | 9/2000 | Shehada | |
| 6,268,603 B1 | 7/2001 | Mullins | |
| 6,272,376 B1 | 8/2001 | Marcu | |
| 6,407,383 B1 | 6/2002 | Byatt | |
| 6,633,043 B2 | 10/2003 | Hegazi | |
| 6,636,577 B1 | 10/2003 | Clarke | |
| 2002/0030812 A1 | 3/2002 | Ortyn et al. | 356/326 |
| 2003/0021331 A1 | 1/2003 | Balla | |
| 2003/0048831 A1 | 3/2003 | Lemoine | |
| 2004/0089804 A1 | 5/2004 | Dantus | |
| 2004/0199079 A1 | 10/2004 | Chuck | |
| 2004/0239924 A1 | 12/2004 | Couderc | |
| 2004/0262501 A1 | 12/2004 | Kajii | |
| 2005/0000812 A1 | 1/2005 | Couderc | |

FOREIGN PATENT DOCUMENTS

| | | |
|---|---|---|
| JP | 9026357 | 1/1997 |
| JP | 2002303578 | 10/2002 |

OTHER PUBLICATIONS

Patra, D. and Mishra, A.K., "Excitation Emission Matrix Spectral Subtraction Fluorescence to Check Adulteration of Petrol by Kerosene," *Applied Spectroscopy*, vol. 55, No. 3, (2001), pp. 338-342.

Hidrovo, C.H. and Hart, D.P. "Emission reabsorption laser induced fluorescence (ERLIF) film thickness measurement," *Measurement Science and Technology*, vol. 12, 467-477 (2001).

\* cited by examiner

APPARATUS AND METHOD FOR MEASURING CONCENTRATIONS OF FUEL MIXTURES USING DEPTH-RESOLVED LASER-INDUCED FLUORESCENCE

CROSS REFERENCE TO RELATED APPLICATION

This application is a division of U.S. application Ser. No. 11/392,814 filed on Mar. 30, 2006 now U.S. Pat. No. 7,846,390.

BACKGROUND OF THE INVENTION

1. Field of the Invention

The present invention relates to fluorescent spectroscopy devices and to methods for quantifying the concentration of components in a mixture of petroleum products, and particularly to an apparatus and method for measuring concentrations of fuel mixtures using depth-resolved laser-induced fluorescence.

2. Description of the Related Art

Fluorescent spectroscopy is a tool that has been used for the qualitative and quantitative analysis of compounds that exhibit the phenomena of fluorescence and phosphorescence. When molecules are irradiated by energy of a particular frequency or wavelength, the electrons experience a transition from the ground state to an excited state due to the absorbance of photons. The electrons return to the ground state by any of several different routes known as deactivation processes. The preferred route is the path that provides the shortest lifetime in the excited state. For certain compounds under appropriate conditions, fluorescence is the preferred deactivation process. Generally, a molecule excited at an absorption frequency will exhibit fluorescence at a lower frequency-longer wavelength emission band. Compounds exhibiting fluorescence usually contain an aromatic functional group or highly conjugated double bond structures, with the intensity increasing with the number of condensed rings per molecule.

Fluorescent spectroscopy takes advantage of these properties. FIG. 14 shows a block diagram of a conventional fluorometer 100 or spectrofluorometer. The fluorometer contains a light source 102, such as a xenon lamp, capable of emitting ultraviolet light (UV). A portion of the light emitted by light source 102 passes through a first monochromator 104 into the sample 106, which is usually contained in a cuvette made from quartz, fused silica, or other material that has a high transmittance to UV radiation. Another portion of the light emitted by light source 102 passes through an attenuator 108 to a reference photomultiplier tube 110, which generates a voltage that provides one input to a differential amplifier 112 or other detector.

The sample 106 emits fluorescent light when transitioning from the excited state to the ground state. The emitted fluorescent light passes to a second monochromator 114 and a sample photomultiplier tube 116, which provides a second input voltage to the differential amplifier 112. The output of the differential amplifier 112 is fed to an analog meter 118, digital readout, plotter or chart recorder, or other output device, which displays the intensity of the fluorescent radiation.

The monochromators include an entrance slit, usually of variable width, and various slits, lenses, mirrors, windows, and a beam dispersal device, usually either a prism or a grating. The monochromator filters or narrows the received light beam to a single frequency or wavelength of interest at a time, and provides for continuously changing the wavelength, usually by rotating the beam dispersal device, the latter process being termed "scanning" the spectrum. Usually the second monochromator is positioned at 90° to the incident light beam from light source 102 in order to minimize the effects of scattering.

In recent years, laser light sources have become available as an alternative to the conventional ultraviolet lamp. Early lasers were limited to a few discrete wavelengths, but dye pulse lasers allow for continuous variation of the wavelength, so that the first monochromator 104 is unnecessary when the light source is a pulsed laser. Conventional fluorometers may be provided with a sample holder turntable that can accommodate more than one cuvette, with the turntable being rotated to place each cuvette successively in the path of the beam from the light source.

The composition of a mixture of fluorescent substances can be analyzed with a conventional spectrofluorometer in the following manner. For each individual component known to be in the mixture, the emission wavelength band is scanned with the excitation wavelength fixed to find maximum intensity. Then, with the emission wavelength fixed at the maximum intensity, the excitation spectrum is scanned for maximum and minimum intensities. The emission spectrum for each of these excitation wavelengths is scanned, and an optimal excitation-emission wavelength pair is selected for that component. Excitation and emission spectra are obtained for the wavelength pairs so selected. For each component, a concentration calibration curve is made from solutions of known concentration at each of the optimal wavelength pairs, which should be linear. The intensity of the unknown mixture is determined at each optimal excitation-emission pair, and the corresponding concentrations of the components in the mixtures can then be determined from the calibration curves.

Fluorescent spectroscopy is particularly useful, when available, due to the sensitivity of detection and the linearity of fluorescent intensity with concentration.

For many reasons, it is necessary to test petroleum products to determine purity and quality. For example, in some areas the more expensive petroleum fuels may be diluted with less expensive petroleum fuels, either intentionally to deceive the purchaser, or unintentionally as the result of contamination in the refining or storage and transport process. While some methods are available for particular analyses, e.g., the separation and quantification of mixtures of fuels having different octane numbers by gas chromatography, such methods are expensive, time consuming, and complicated.

Petroleum products are known to exhibit fluorescence. However, petroleum fuels, such as kerosene, gasoline, and diesel fuel, are each composed of mixtures of different hydrocarbons that fall within certain boiling point ranges loosely coordinated with molecular weight ranges. The type and distribution of hydrocarbons within each class of fuel may also vary according to the geographical source of the crude oil and the type of refining method (distillation, cracking, etc.). Petroleum products are dense, contain mixtures of hydrocarbons having overlapping excitation-emission spectra so that fluorescent emissions may be reabsorbed, and also may be contaminated with quenching compounds. For these reasons, fluorescent spectroscopy is not widely used in the industry.

Nevertheless, several efforts have been made to apply spectrofluorometric methods for quantitative and qualitative analysis of petroleum products. Patra and Mishra report the use of synchronous fluorescent scan spectroscopy, in which both excitation and emission monochromators are scanned simultaneously while keeping a fixed wavelength interval between them, to analyze mixtures of petrol, diesel and kerosene in *The Analyst*, Vol. 125, pp. 1383-1386 (2000). Patra and Mishra also report a technique using a 3-dimensional emission/excitation intensity contour diagram or matrix and the subtraction of spectral volumes to evaluate the adulteration of petrol by kerosene in *Applied Spectroscopy*, Volume 55, Number 3, pp. 338-342 (2201). Hidrovo and Hart describe a technique for measuring the thickness of an oil film utilizing the reabsorption and emission of two fluorescent dyes by emission reabsorption laser induced fluorescence in *Measurement Science and Technology*, Vol. 12, pp. 467-477 (2001).

However, none of the above apparatus and methods, taken either singly or in combination, is seen to describe the instant invention as claimed. Thus, an apparatus and method for measuring concentrations of fuel mixtures using depth-resolved laser-induced fluorescence solving the aforementioned problems is desired.

SUMMARY OF THE INVENTION

The apparatus for measuring concentrations of fuel mixtures using depth-resolved laser-induced fluorescence is a fluorometer equipped with a sample container holder that is movable in the path of the beam from the light source. Fluorescent emissions from the sample mixture pass at 90° to the excitation light path through a slit that is narrow enough that the emission intensity is effectively produced by a thin layer of the sample and focused on an emission monochromator, with successive thin layers receiving nonuniform excitation radiation due to reduction of intensity along the excitation light source path with increasing depth penetration and due to reabsorption of emitted fluorescence from adjacent layers. The method has a first mode in which the emission spectrum is scanned at a fixed depth, and a second mode in which the sample is moved relative to the emission monochromator slit to vary the depth while keeping the emission wavelength fixed.

The excitation light source is preferably a pulsed dye laser, although a UV lamp with an excitation monochromator may be used. Translation of the sample may be accomplished in any desired manner. For example, the sample container, typically a standard cuvette, may be mounted on a Plexiglass® (Plexiglas is a registered trademark of Rohm & Haas Co.) plate. The Plexiglas plate is mounted on a linear translation stage controlled by a stepper motor that moves the plate along the path of the excitation light beam in discrete increments, so that the slit in the emission monochromator is opposite the cuvette at a precisely measured depth of penetration of the excitation light beam into the sample container.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
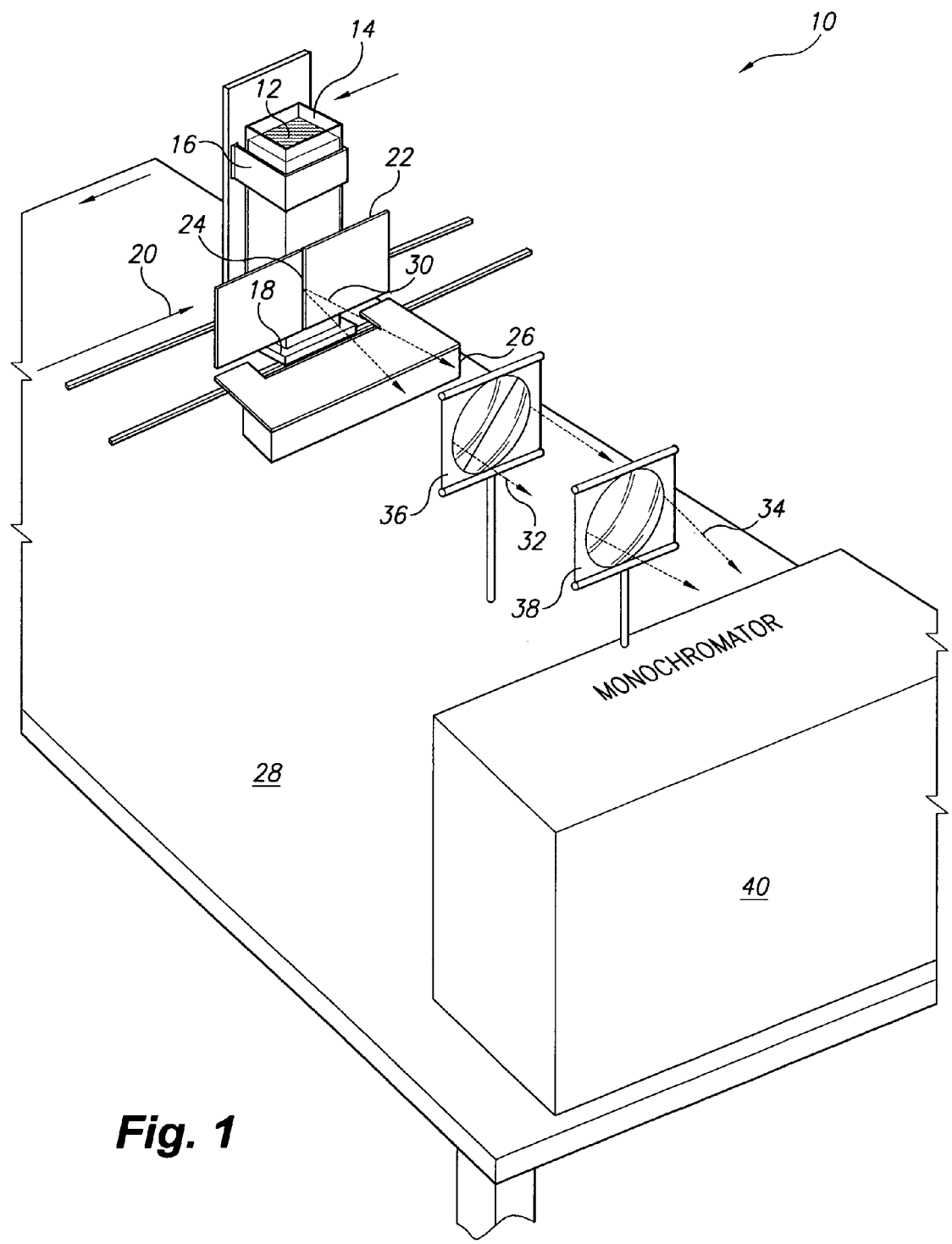
FIG. 1 is a diagrammatic view of a movable stage of an apparatus for measuring concentrations of fuel mixtures using depth-resolved laser-induced fluorescence according to the present invention.
Figure 2:
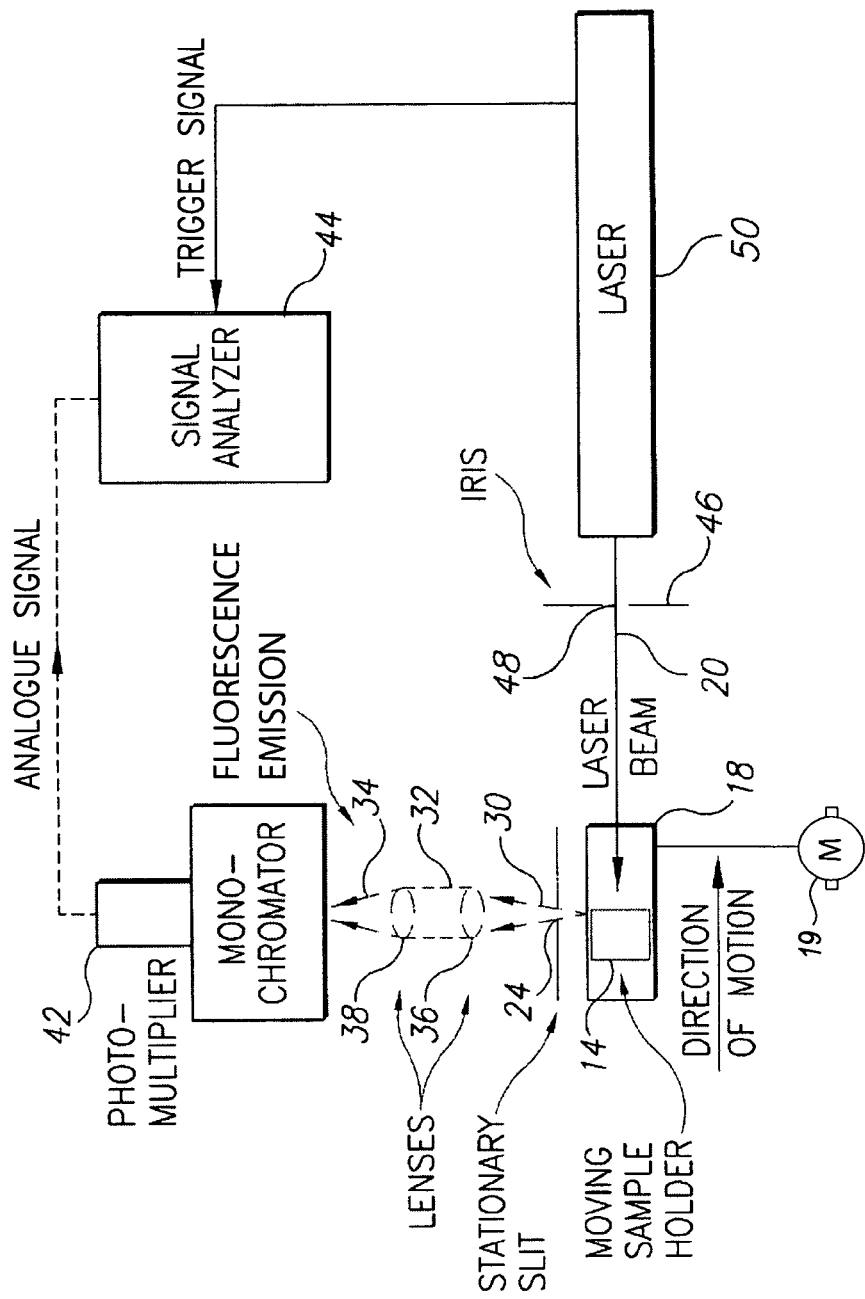
FIG. 2 is a block diagram of the apparatus for measuring concentrations of fuel mixtures using depth-resolved laser-induced fluorescence according to the present invention.

With reference to FIGS. 1 and 2, the apparatus 10 for measuring concentrations of fuel mixtures using depth-resolved laser-induced fluorescence performs measurements on a sample container 14 holding a fluid sample 12, which may be, for example, a fuel mixture. The sample container 14 is formed from an optically transparent and chemically inert material, such as quartz, fused silica, or other material having a high transmittance to ultraviolet radiation (UV) and may be in the form of a conventional cuvette, test tube or the like. In a preferred embodiment, sample container 14 is a quartz cuvette having a length of approximately one centimeter, a width of approximately one centimeter, and a height of approximately five centimeters.

The sample container 14 (hereafter sample container or container), containing fluid 12, is mounted on a translatable stage 18, which moves linearly along a first axis. The translatable stage 18 may be L-shaped, including a vertical support and a horizontal support. The translatable stage may be formed from Plexiglas plates or any other suitable material, and holds container 14 through use of a fastener 16, such as a clamp, a flexible, elastic band, or other suitable releasable fastener. Hereafter, the translatable stage is referred to as the sample holder.

Sample holder 18 may be made to move in the path 20 of the excitation light beam in any desired manner. Preferably, the horizontal support of sample holder 18 is mounted on a track and is actuated to move along the track by stepper motor 19. Stepper motor 19 moves the sample holder 18 in defined increments of about 0.16 mm. Alternatively, sample holder 18 may be provided with mechanical means for moving the sample container 14 in the path 20 of the excitation light beam. For example, the horizontal support of the sample holder may have a rack mounted thereon operated by a pinion or gear train operable by a Vernier dial, a thumbwheel, a slider or the like, which may be equipped with a precision scale or with detents corresponding to 0.16 mm increments of movement in the path of the beam.

As shown in FIG. 2, sample holder 18 moves towards laser 50, so that the distance between the sample container 14 and the laser 50 increases or decreases during measurement, according to the depth measurements desired. It should be understood that apparatus 10 may have any suitable light source capable of fluorescing fluid mixture 12. However, in the preferred embodiment, a pulsed dye laser is utilized to generate a single-frequency coherent beam, thus reducing the occurrence of backscattering of unwanted frequencies of light. Alternatively, an ultraviolet lamp, such as a Xenon lamp with a monochromator to adjust the excitation wavelength, may be used in place of laser 50. Stepper motor 19 may move sample holder 18 at any desired speed. However, in the preferred embodiment, sample holder 18 is moved to produce a resolution of approximately 3.8 increments per mm.

As shown in FIG. 2, laser 50 generates a laser beam 20, which travels along the first axis to penetrate transparent sample container 14 and generate fluorescence within fuel mixture 12. Laser beam 20 may be shaped and directed by a conventional optical iris 48, formed through a screen 46, as shown. Iris 48 is selected for a desired-beam diameter, depending upon the needs of the user. As best shown in FIG. 1, translatable stage 18 moves with respect to support surface 28, which may be, for example, an optical bench, an enclosed fluorometer housing, or the like. A diffraction screen 22 is mounted on support surface 28, so that translatable stage 18 also moves with respect to screen 22.

Screen 22 has a vertical slit 24 formed therethrough for diffracting the fluoresced light emitted by the fluid mixture 12. The diffracted light beam (illustrated by dashed arrows 30) passes along a second axis, substantially orthogonal to the first axis, and impinges upon a collimating lens 36 to form a relatively and substantially unidirectional light beam 32. Light beam 32 passes through a focusing lens 38 to form a focused beam 34, which is received by monochromator 40. Lenses 36, 38 may be any suitable lenses. However, in the preferred embodiment, lenses 36, 38 are convex quartz lenses. The fluorescent emission is depth-resolved in that only the florescence from a particular depth within container 14 passes through the stationary slit 24 to the frequency separator 40, so that, in theory, only the fluorescence emitted by a thin vertical layer of the mixture in cuvette 14 passes through slit 24.

An exemplary monochromator 40 is the f/3.4 Applied Photophysics® monochromator. Each frequency component is passed to photomultiplier assembly 42, which includes at least one photomultiplier tube, for producing an amplified analog signal associated with each frequency component. Photomultiplier 42 is preferably a fast photomultiplier. One such exemplary fast photomultiplier is the Hamamatsu® R1564U-07 photomultiplier.

Each analog signal is received by a signal analyzer 44, which measures the relative intensities of each frequency component in order to determine the chemical composition of fluid 12. Signal analyzer 44 further digitizes the analog signals. One such exemplary signal analyzer is the EG&G® Model 4402 Signal Processor. Each chemical composition contained within fluid mixture 12 produces a particular wavelength spectra under fluorescence. Thus, an analysis of the intensities at the wavelengths produced by scanning the monochromator 40 reveals the chemical components and their relative proportions within the mixture.

It should be noted that laser 50 may be a pulsed laser or a continuous laser. If a pulsed laser is utilized, then signal analyzer 44 is preferably triggered by the Q-switch of the laser 50. As shown in FIG. 2, the laser 50 may be in electrical communication with the signal analyzer 44. Laser 50 generates a trigger signal so that signal analyzer 44 has an appropriate excitation signal to compare to the corresponding emission signal from photomultiplier tuber 42. One such exemplary laser is a pulsed fourth harmonic YAG laser, having a wavelength of 266 nm. For such a laser, preferably the energy output is held at a fixed value of 5 mJ or 4 mJ, though other energy ranges may be utilized.

Signal analyzer 44 may analyze signals for each position along the first axis through which stage 18 moves, or may include an averaging routine to average the signals over the entire movement of the stage.

When a fluorescing liquid sample, such as the fuel oil 12 in container 14, is irradiated with UV radiation, it emits light at a wavelength longer than that of the excitation wavelength. The characteristics of the emitted fluorescence spectrum, i.e., its shape, spectral region, temporal behavior, etc., depend not only on the type and the concentrations of the individual chemical compounds, but also on the geometry of the sample illumination. The bulk of the liquid sample, which may be modeled as a succession of thin layers, each stacked upon the other, receives non-uniform excitation radiations at each layer and, consequently, each layer emits a distinct fluorescence spectrum. The non-uniform excitation radiations associated with each layer occur mainly because of the reduction in the intensity of the excitation laser radiation with path length as the laser light beam penetrates inside the sample, and also because of the reabsorption of the already emitted fluorescence from the adjacent layers caused by the fluorescent emission of one compound occurring at the excitation wavelength of a second compound.

It should be noted that, in general, fluorescence emission from within a fluid mixture is non-uniform, due to inhomogeneous emission-reabsorption fluorescence effects. The movable sample container 14 is utilized in order to monitor the variations in the non-uniform fluorescence emissions by either scanning the monochromator 40 emission wavelengths, or by scanning the sample container 14 depth of penetration of the excitation beam from one end to the other. Due to the ability to scan over the movement of the sample container 14, apparatus 10 is able to detect minute differences in the concentration of the fuel mixture 12, particularly for oil mixtures, with high accuracy.

The apparatus 10 may be utilized in two different modes. In the first mode, the sample container 14 is fixed at a desired depth setting and the monochromator is scanned to obtain the emission spectrum. For the exemplary devices, dimensions and wavelengths given above, the monochromator has a slit size of approximately 1.5 mm and is scanned in the region between 280 nm and 620 nm with a speed of 1.6 nm per second. The second mode is achieved by fixing the monochromator 40 at a particular emission wavelength setting and scanning the sample container 14 from one end to the other to detect fluorescent intensity from successive thin layers at progressively increasing depths of penetration of the excitation beam. In this mode, and given the same exemplary figures as given above, the stepper motor is chosen so that each point in the signal analyzer 44 corresponds to 0.16 mm translation of the sample holder 18 by the stepper motor 19.

For convenience, in the following examples, the depth is described in terms of point numbers. The distance between two point numbers is 0.16 mm. Therefore, depths at point numbers 9, 10, 11, 12, and 13, for example, correspond to distances of 1.44 mm, 1.60 mm, 1.76 mm, 1.92 mm, and 2.08 mm, respectively, from the front surface of the cuvette.

Further, the fuel oils used in the following examples, i.e., kerosene, diesel oil, and gasoline, were all in pure form without any additives. They were mixed by means of pipettes and grouped into three sets of different concentration ranges (in % v/v) for the kerosene and diesel oil mixtures, one set for the gasoline and diesel oil mixtures, and one set for mixtures of gasoline having octane (95) with gasoline having octane (91) as follows:

Set 1: (K %:D %)=(100:0), (99:1), (98:2), (97:3), and (95:5);

Set 2: (K %:D %)=(90:10), (80:20), (70:30), (50:50), (30:75), and (10:90);

Set 3: (K %:D %)=(5:95), (3:97), (2:98), (1:99), and (0:100);

Set 4: (G %:D %)=(100:0), (99:1), (98:2), (97:3), and (95:5);

Set 5: (Octane (95) %:Octane (91) %)=(100:0), (90:10), (80:20), and (0:100);

where K, D, and G refer to kerosene, diesel fuel, and gasoline, respectively.

Example 1

Kerosene Contaminated with Minute Concentrations of Diesel Fuel (Sample Data and Analysis)

This example first shows the types of spectroscopic data acquired by the method. This is done in both modes of operation for the (K:D=95:5) mixture. Then, the complete mixtures of Set 1 are considered in the same manner, followed by demonstrations of possible ways for constructing calibrations curves to predict the concentrations.

Figure 3:
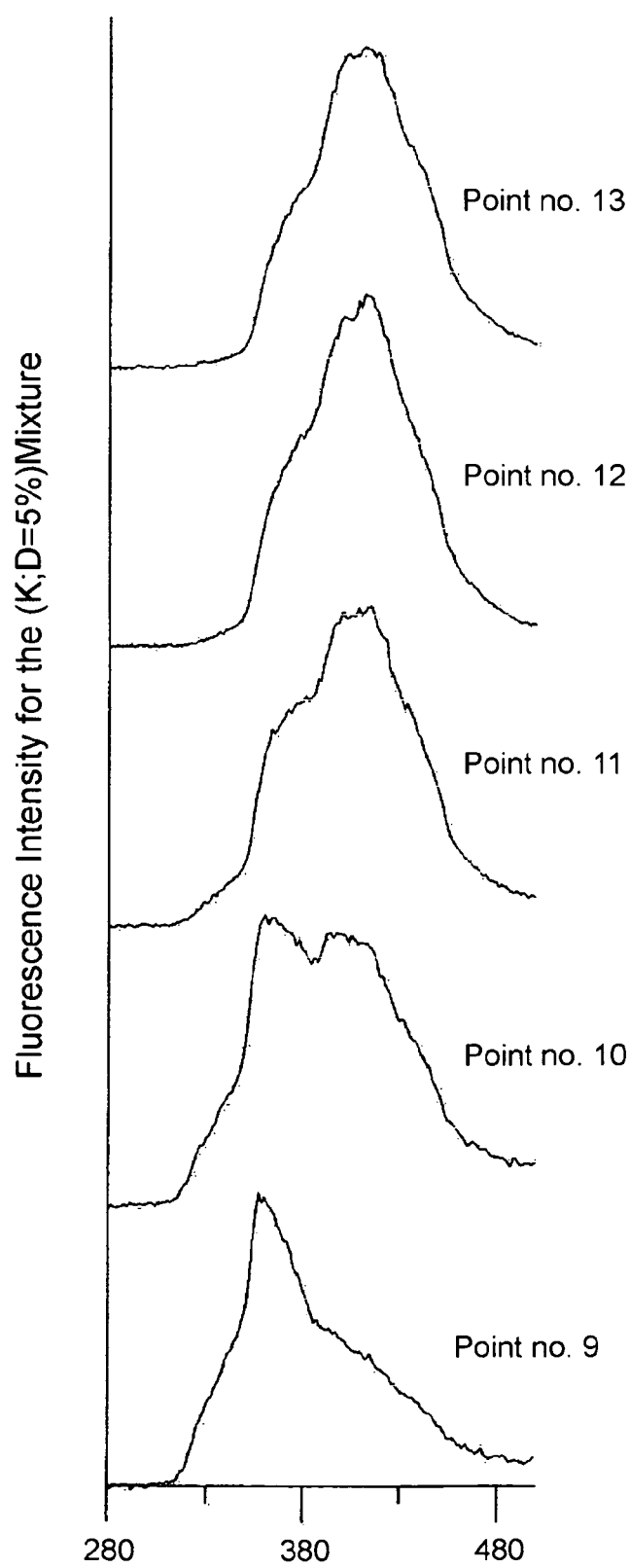
FIG. 3 is a graph of the emission spectra of a 95:5 (% v/v) kerosene:diesel oil mixture at various depth settings according to the apparatus and method for measuring concentrations of fuel mixtures using depth-resolved laser-induced fluorescence of the present invention.

Referring to FIG. 3, there are shown depth-resolved emission spectra for the (K:D=95:5) mixture at depths of point numbers 9 through 13. They were collected by scanning the monochromator at these fixed depths (first mode of operation). It can be seen that the spectra vary dramatically with depth. This variation is mainly due to the emission reabsorption effect as described above. The deeper the location from which the emitted fluorescence is monitored, the more the emission spectra shift toward longer wavelengths, indicating that there is a gradual transfer of energy between the compounds of the mixture with depth. This phenomenon depends on the types of mixtures in use. When the concentrations in the mixture are slightly changed, the spectra will also change slightly, a result that can be utilized to determine minute changes in the concentrations.

Figure 4:
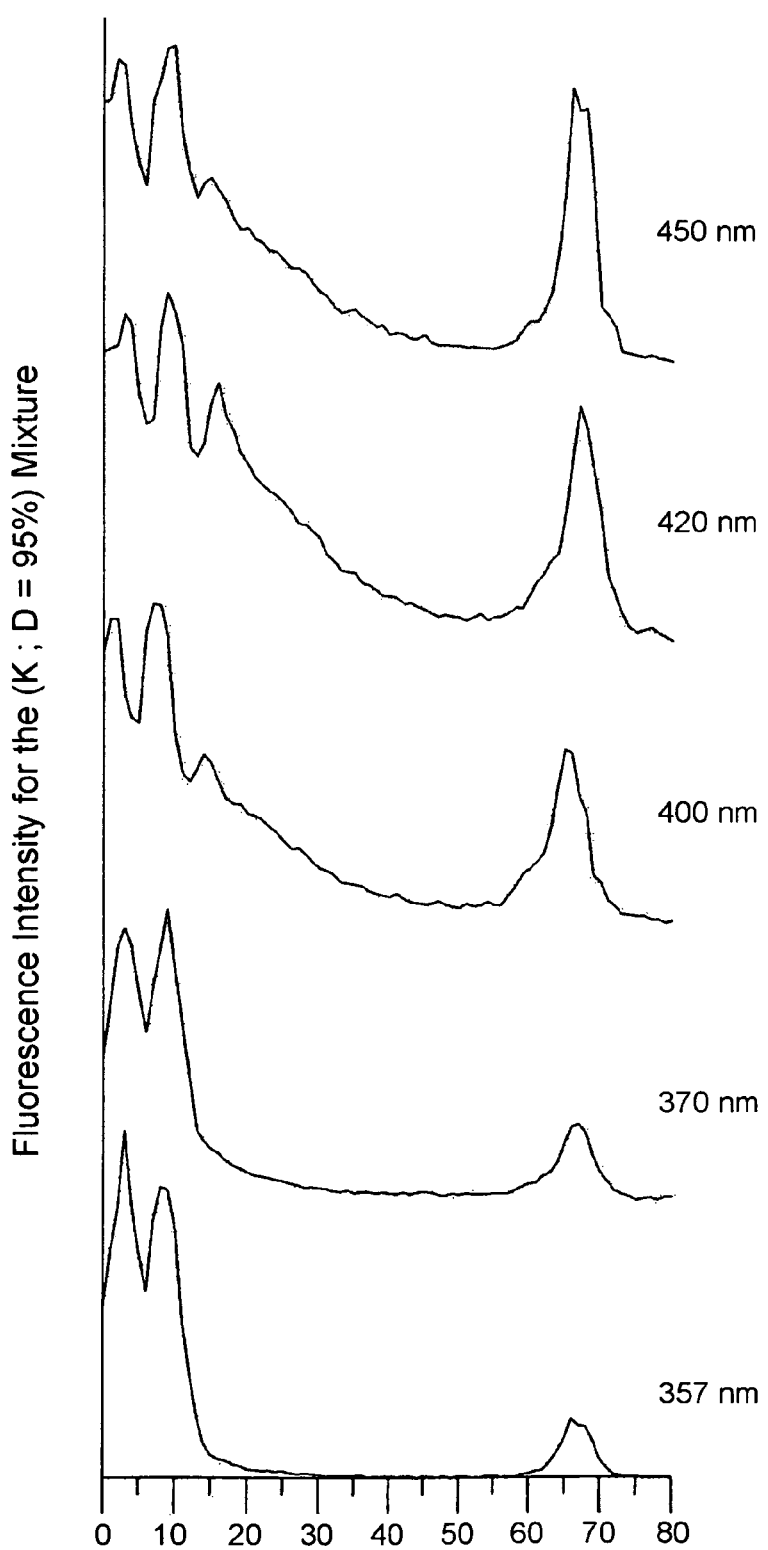
FIG. 4 is a graph showing fluorescent intensity vs. depth at selected emission wavelengths of a 95:5 (% v/v) kerosene: diesel oil mixture according to the apparatus for measuring concentrations of fuel mixtures using depth-resolved laser-induced fluorescence of the present invention.

Referring to FIG. 4, there are shown fluorescence intensity versus depth diagrams for the (K:D=95:5) mixture. These data were acquired by fixing the monochromator at particular wavelength settings and scanning the sample holder as described above (second mode of operation). The energy of the laser pulse is kept fixed at 5 mJ. The wavelength settings are chosen to correspond to the maxima (or peaks) observed in the spectra of FIG. 3, namely, 357 nm, 370 nm, 400 nm, 420 nm, and 450 nm. The x-axis corresponds to the distance between the front of the illuminated cuvette surface and the depth at which the emitted fluorescence is monitored (each point number corresponds to a distance of 0.16 mm), while the y-axis corresponds to the intensity of the emitted fluorescence at specific single wavelengths (all intensities are normalized at the second peak corresponding to point no. 9). The first and last peaks in each of these diagrams are due to scatterings from the front and back walls of the quartz cuvette, respectively, and are not considered in this analysis.

It can be seen in FIG. 4 that the fluorescence intensity at 357 nm dies quickly with depth, indicating that there has been some energy transfer from the original excitation wavelength at 266 nm to lower energy levels corresponding to the 357 nm, but all of this occurs in approximately the first 3.2 mm inside the cuvette. This is also the case for the 370 nm fluorescence intensity. However, energy transfer to even lower levels, corresponding to longer fluorescence emission wavelengths, takes place through deeper distances inside the cuvette, as can be seen by examining the variation of the fluorescence intensities at 400 nm, 420 nm, and 450 nm with depth. Wavelength-filtered intensity variations of this sort can also be utilized to identify the types and concentrations of mixtures. It should be noted that in this second mode of operation, the mode does not involve any scanning of the monochromator other than having it set at a particular wavelength.

It should be further noted that the wavelength-filtered fluorescence intensity variation with depth also depends on the types and concentrations of the mixtures. For the kerosene/diesel fuel mixture, it is clear that by monitoring this variation dependence at 420 nm produces a distinct peak near point no. 15 (approximately 2.40 mm from the outer surface of the cuvette), which becomes very prominent. This is again due to a combination of factors, one of which is the fluorescence emission reabsorption of that particular mixture.

Figure 5A:
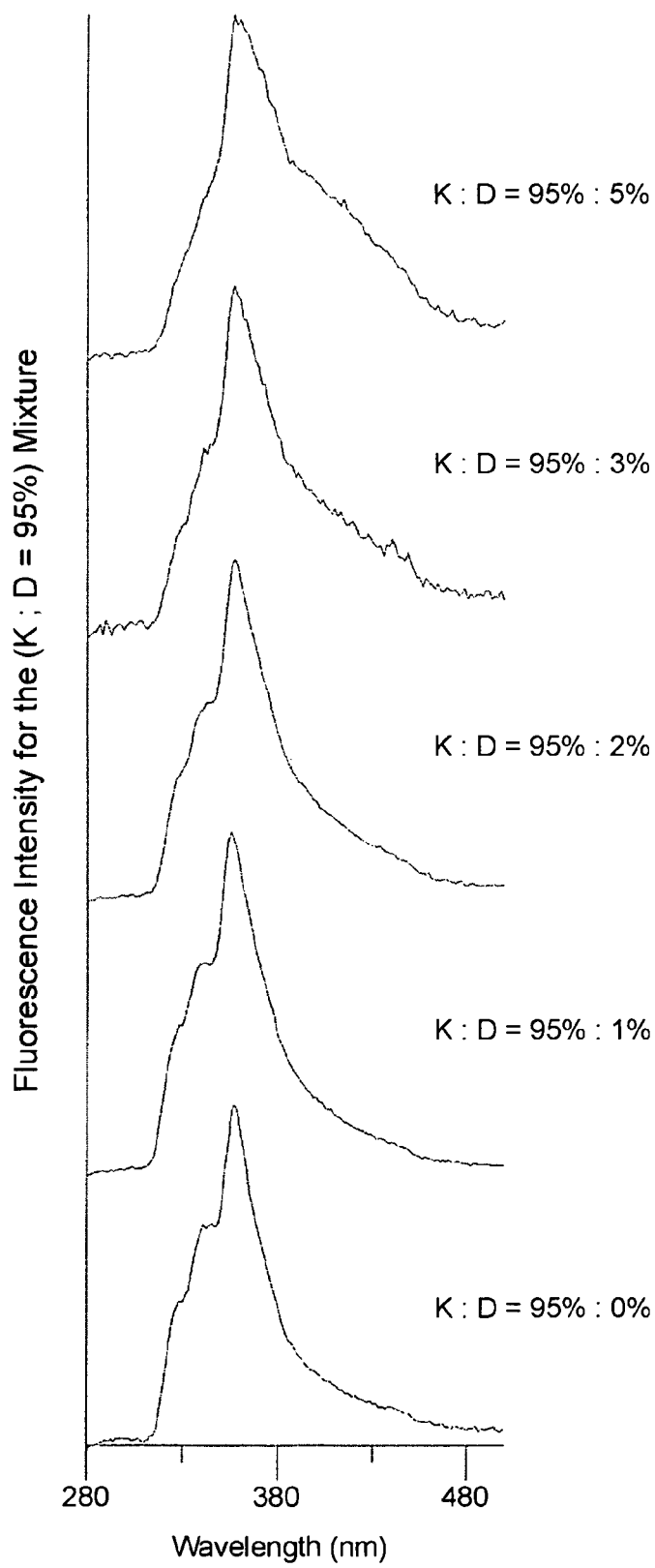
FIG. 5A is the emission spectra of selected mixtures of kerosene and diesel fuel at a depth of 9 points (1.44 mm) according to the apparatus and method for measuring concentrations of fuel mixtures using depth-resolved laser-induced fluorescence of the present invention.
Figure 5B:
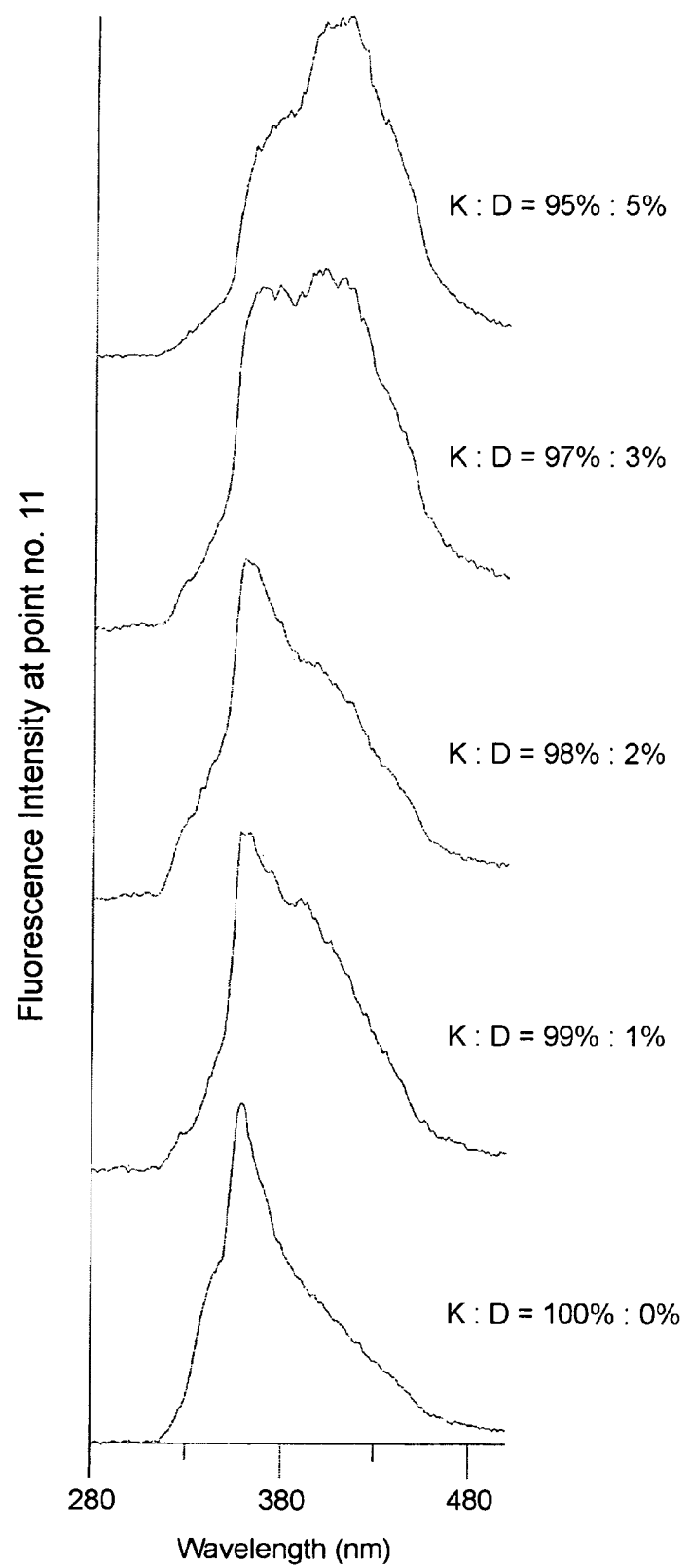
FIG. 5B is the emission spectra of selected mixtures of kerosene and diesel fuel at a depth of 11 points (1.76 mm) according to the apparatus and method for measuring concentrations of fuel mixtures using depth-resolved laser-induced fluorescence of the present invention.
Figure 5C:
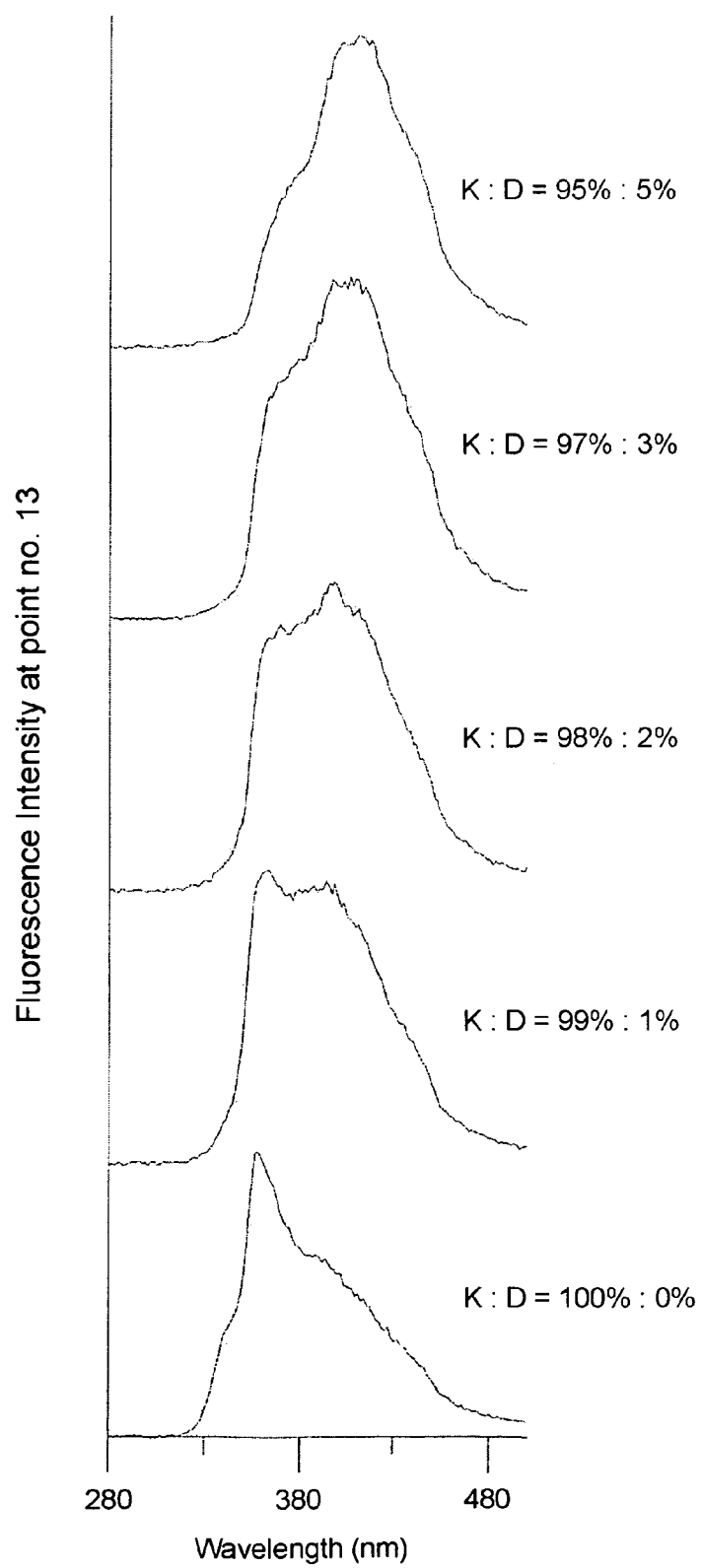
FIG. 5C is the emission spectra of selected mixtures of kerosene and diesel fuel at a depth of 13 points (2.08 mm) according to the apparatus and method for measuring concentrations of fuel mixtures using depth-resolved laser-induced fluorescence of the present invention.

Having introduced the types of spectroscopic data this method produces, the method can now be implemented in the identification of the kerosene/diesel fuel mixtures of Set 1. Referring to FIGS. 5A, 5B, and 5C there are shown emission spectra for the kerosene/diesel fuel mixtures having concentrations of (K:D)=(100:0), (99:1), (98:2), (97:3), and (95:5) measured at the three point nos. 9, 11, and 13, respectively. The spectra have been measured using the first mode of operation. It can be seen that the shift toward longer wavelength increases with concentration at all three points, but with more dramatic effect for the eleventh and thirteenth point numbers. It can be seen also that there are two distinct maxima in the spectra, one at 357 nm and the other at about 400 nm. The ratio of these two peaks can be used as an indication of the amount of diesel fuel that contaminates the kerosene.

Figure 5D:
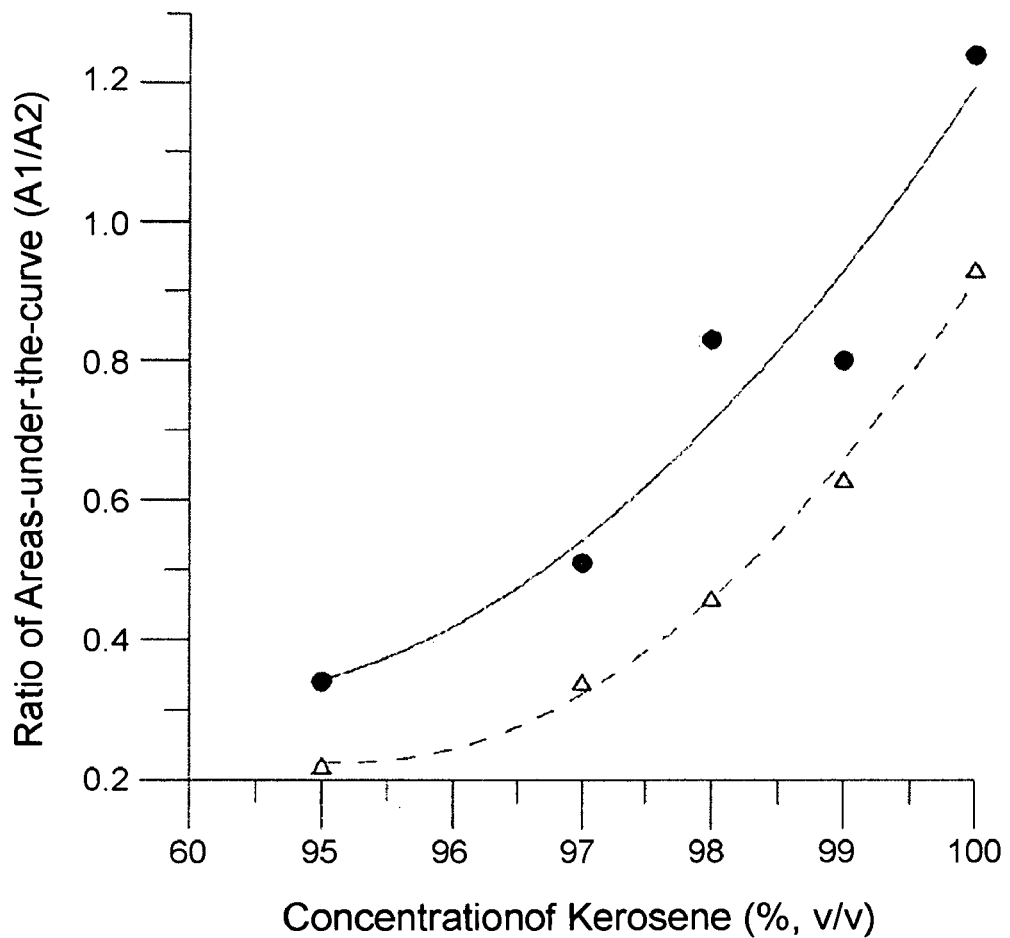
FIG. 5D is a graph showing possible calibration curves for the concentration of kerosene drawn from the emission spectra of FIGS. 5B (the solid line curve) and 5C (the dashed line curve), respectively, according to the apparatus and method for measuring concentrations of fuel mixtures using depth-resolved laser-induced fluorescence of the present invention.

Referring to FIG. 5D, there is shown possible calibration curves relating the ratios of the areas-under-the-curve $A_1/A_2$ as functions of concentration, where $A_1$ and $A_2$ are the area-under-the-curves from 340 nm to 380 nm and from 380 nm to 450 nm, respectively. The curves have been constructed from the data of FIGS. 5B and 5C. It is clear that the curves can distinguish between mixtures having diesel oil concentration variations of less than 0.5%. It should be mentioned that such calibration curves are just two possible examples of how the data of the depth-resolved emission spectra can be used to measure the concentrations of the mixture in these particular mixtures. Other areas could also be possible.

Figure 6A:
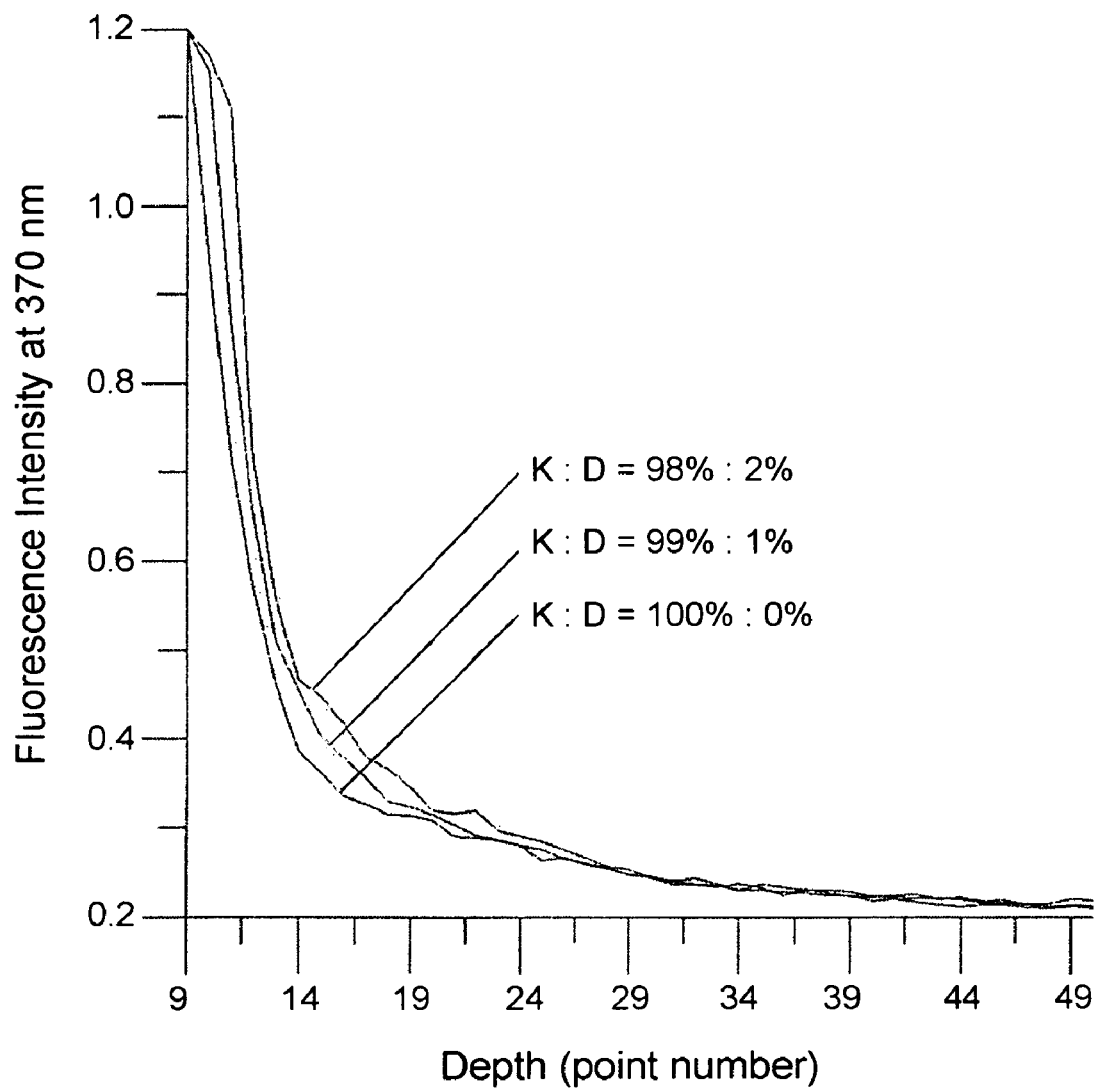
FIG. 6A is a plot of fluorescent intensity vs. depth for selected mixtures of kerosene and diesel oil (diesel oil 0-5%) at an emission wavelength of 370 nm according to the apparatus and method for measuring concentrations of fuel mixtures using depth-resolved laser-induced fluorescence of the present invention.
Figure 6B:
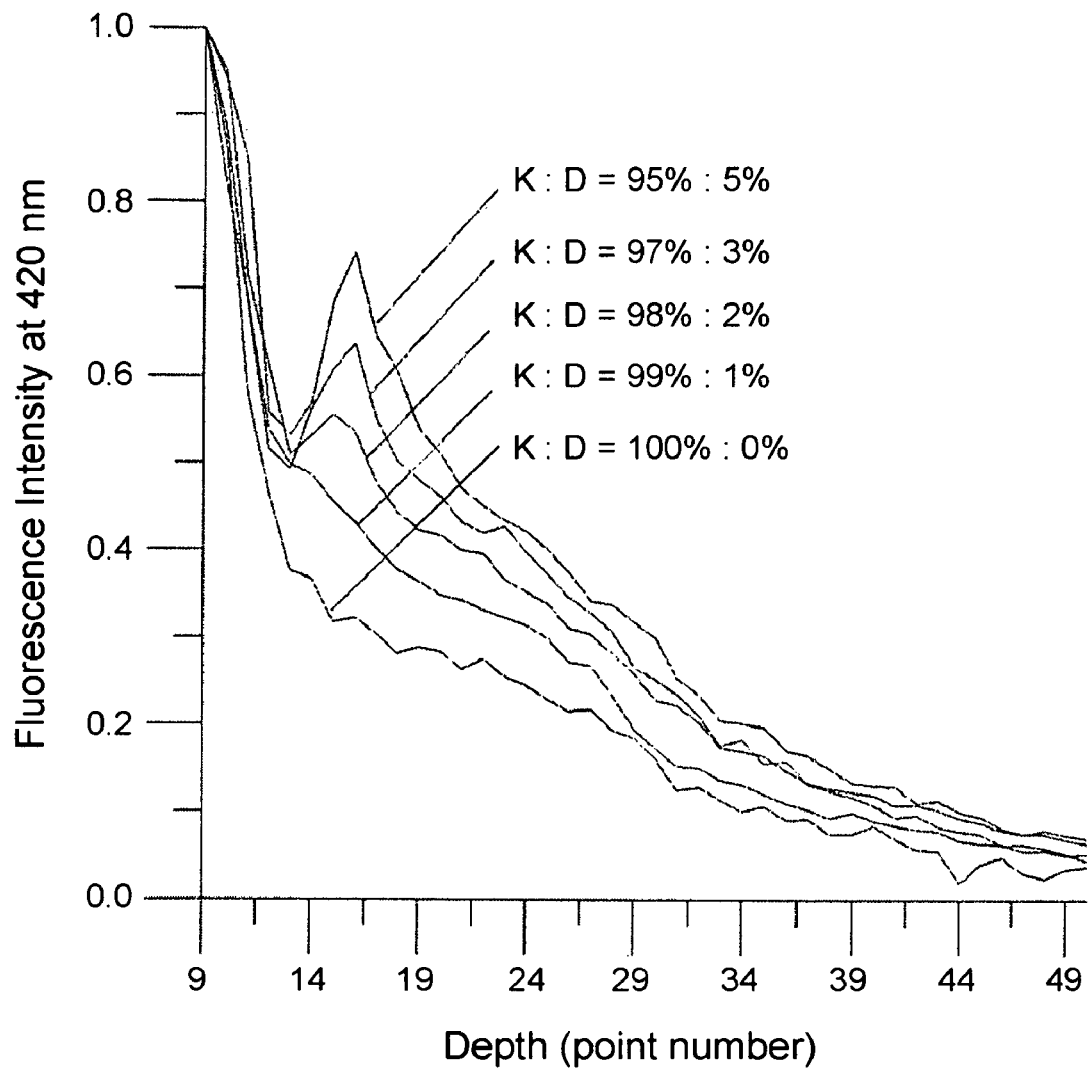
FIG. 6B is a plot of fluorescent intensity vs. depth for selected mixtures of kerosene and diesel oil (diesel oil 0-5%) at an emission wavelength of 420 nm according to the apparatus and method for measuring concentrations of fuel mixtures using depth-resolved laser-induced fluorescence of the present invention.
Figure 6C:
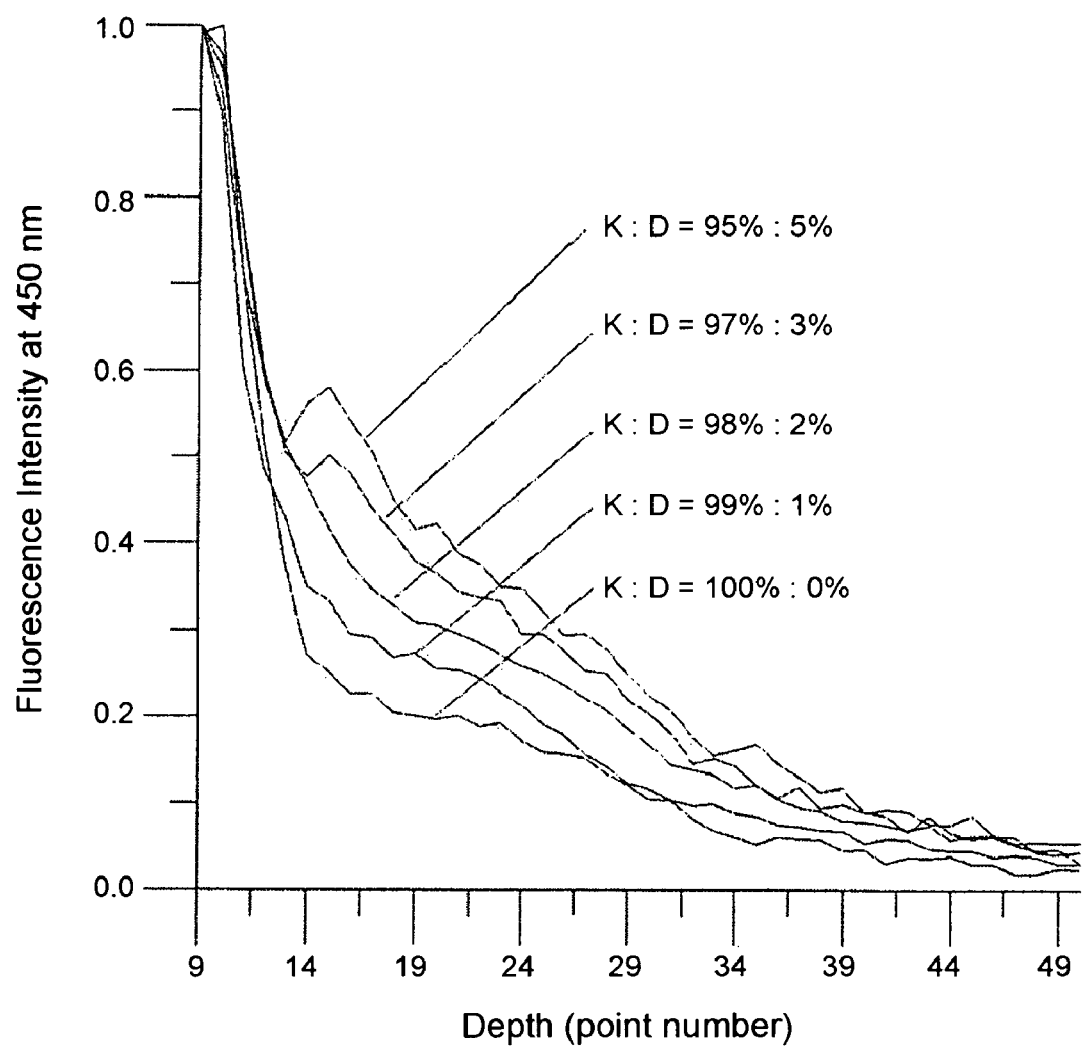
FIG. 6C is a plot of fluorescent intensity vs. depth for selected mixtures of kerosene and diesel oil (diesel oil 0-5%) at an emission wavelength of 450 nm according to the apparatus and method for measuring concentrations of fuel mixtures using depth-resolved laser-induced fluorescence of the present invention.

Now referring to FIGS. 6A, 6B, and 6C, there are shown data collected using the second mode of operation at three wavelengths 370 nm, 420 nm, and 450 nm, respectively, for the (K:D)=(100:0), (99:1), (98:2), (97:3), and (95:5) concentrations. They represent intensities of the emitted fluorescence at these wavelengths when measured as functions of depth. The plots are all normalized at the maximum intensity observed at point no. 9, and they are all shown in sections between point nos. 9 and 50 (corresponding to depths between 1.44 mm and 8.00 mm). It can be seen that, as the concentration of the diesel fuel increases, the intensities at the selected emission wavelengths also increase throughout the depth of the cuvette. The dramatic effect, however, takes place for the fluorescence emissions at 420 nm and 450 nm only, and not for the 370 nm. There is also the prominent peak near point no. 15, which clearly appears to also increase with diesel concentration. The intensities in these plots can be also utilized to determine minute changes in the mixtures' concentrations.

Figure 6D:
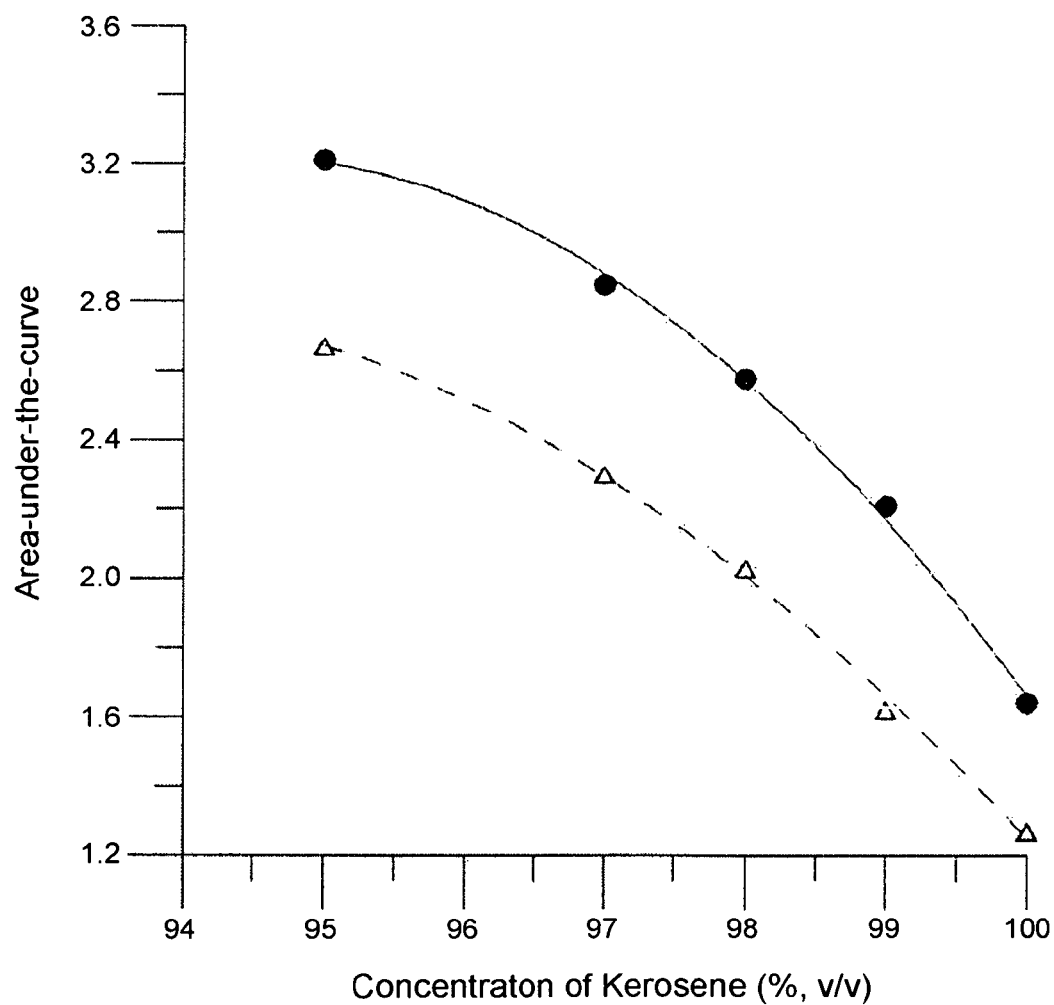
FIG. 6D is a graph showing possible calibration curves for the concentration of kerosene drawn from the intensity vs. depth data of FIGS. 6B (the solid line curve) and 6C (the dashed line curve), respectively, according to the apparatus for measuring concentrations of fuel mixtures using depth-resolved laser-induced fluorescence of the present invention.

Referring to FIG. 6D, there is shown two of the possible calibration curves. These were constructed by measuring the areas under the prominent peaks near point no. 15; in particular, the areas between point nos. 14 and 19, as functions of concentrations. These calibration curves utilized the two cases of FIGS. 6B and 6C, and have been constructed after the peaks at point nos. 9 have all been normalized to unity. It is clear also that these calibration curves can distinguish between mixtures having diesel oil concentration variations of less than 0.5%.

Example 2

Kerosene and Diesel Mixtures in the Range from 10% to 90%

The second example considers the kerosene/diesel fuel mixtures of Set 2, which has concentrations of (K %:D %)=

(90:10), (80:20), (70:30), (50:50), (30:75), and (10:90), and focuses on the second mode of operation only. The effect of varying the laser intensity and the size of the slit of moving sample holder on the observed diagrams are also investigated. The laser energy per pulse used in this example is 4 mJ, as opposed to 5 mJ that was used in the previous example.

Figure 7A:
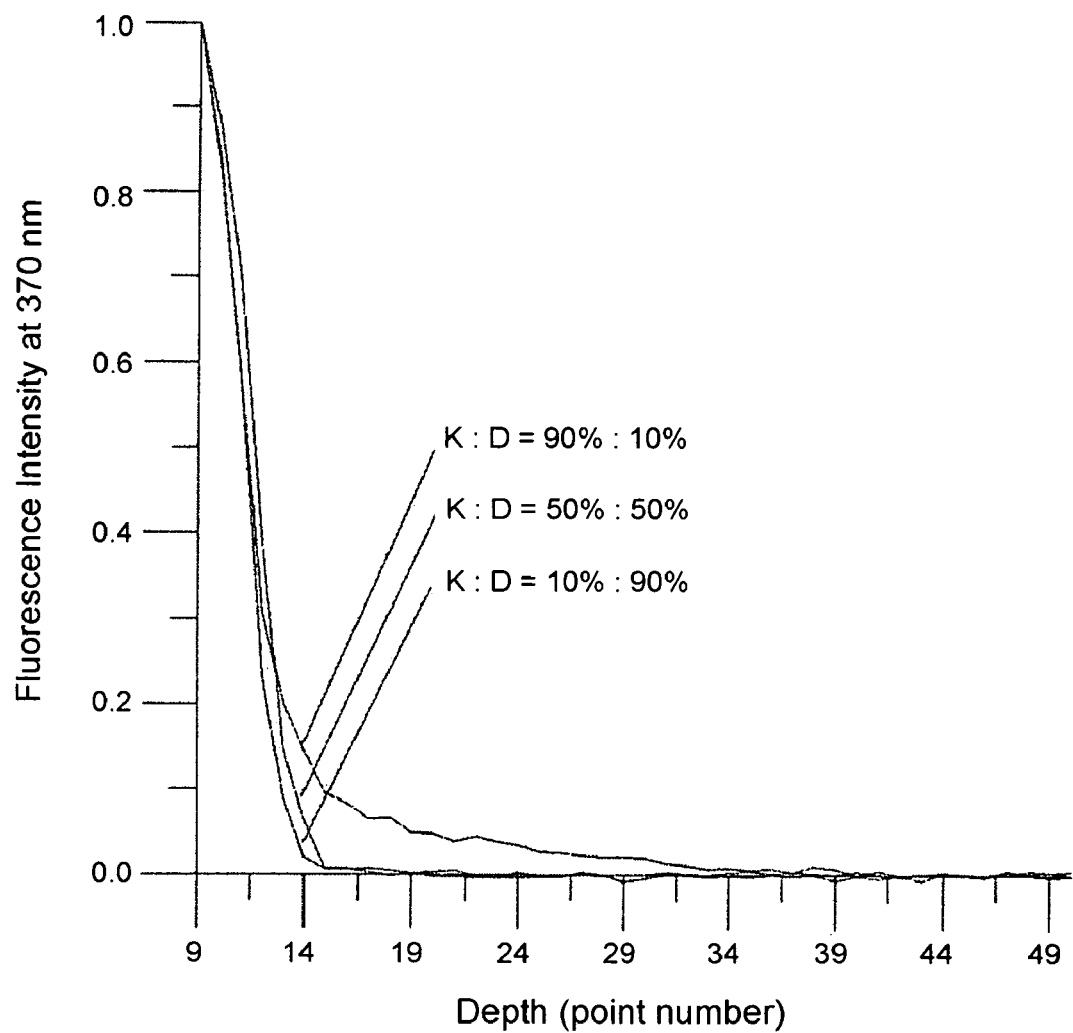
FIG. 7A is a plot of fluorescent intensity vs. depth for selected mixtures of kerosene and diesel oil (diesel oil 10-90%) at an emission wavelength of 370 nm according to the apparatus and method for measuring concentrations of fuel mixtures using depth-resolved laser-induced fluorescence of the present invention.
Figure 7B:
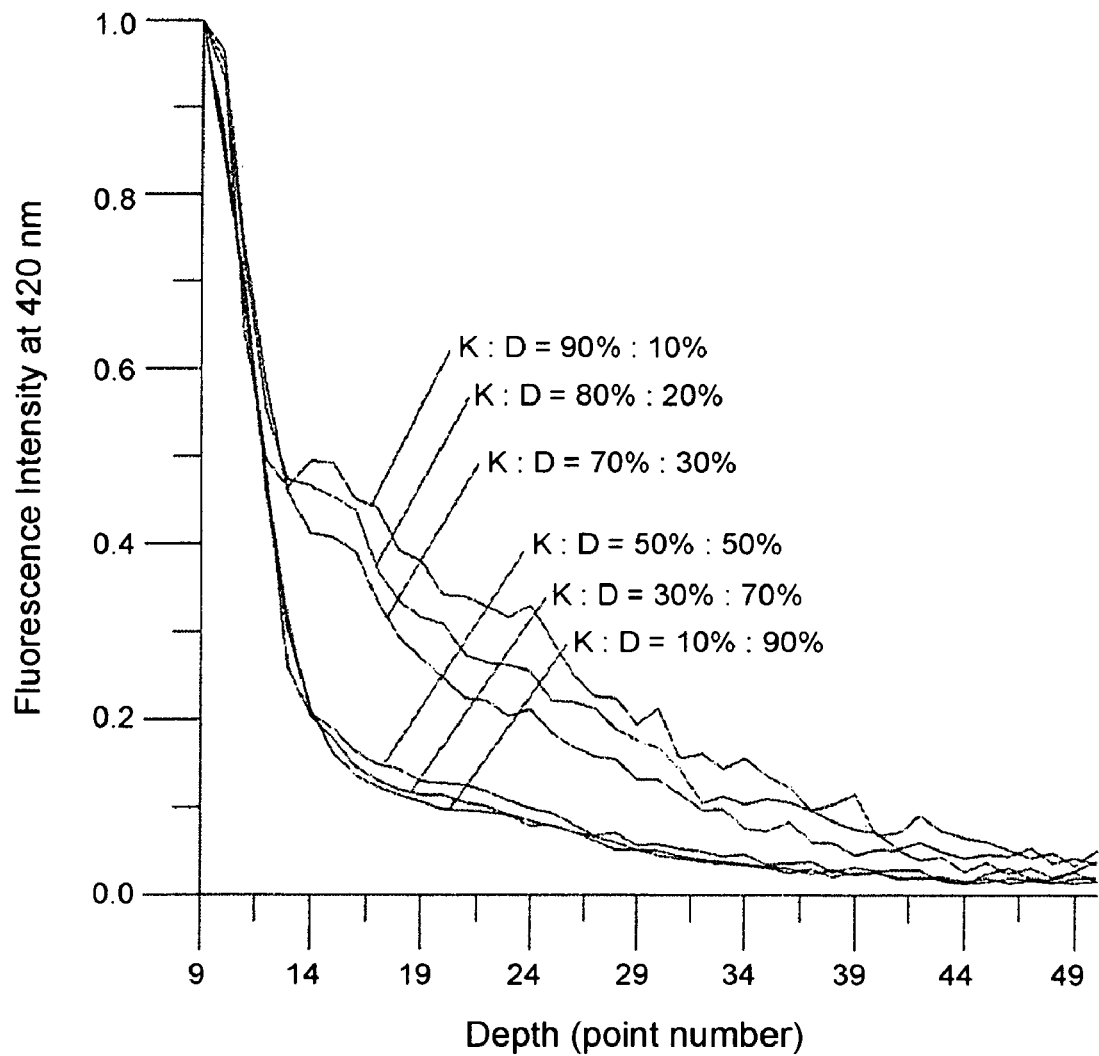
FIG. 7B is a plot of fluorescent intensity vs. depth for selected mixtures of kerosene and diesel oil (diesel oil 10-90%) at an emission wavelength of 420 nm according to the apparatus and method for measuring concentrations of fuel mixtures using depth-resolved laser-induced fluorescence of the present invention.
Figure 7C:
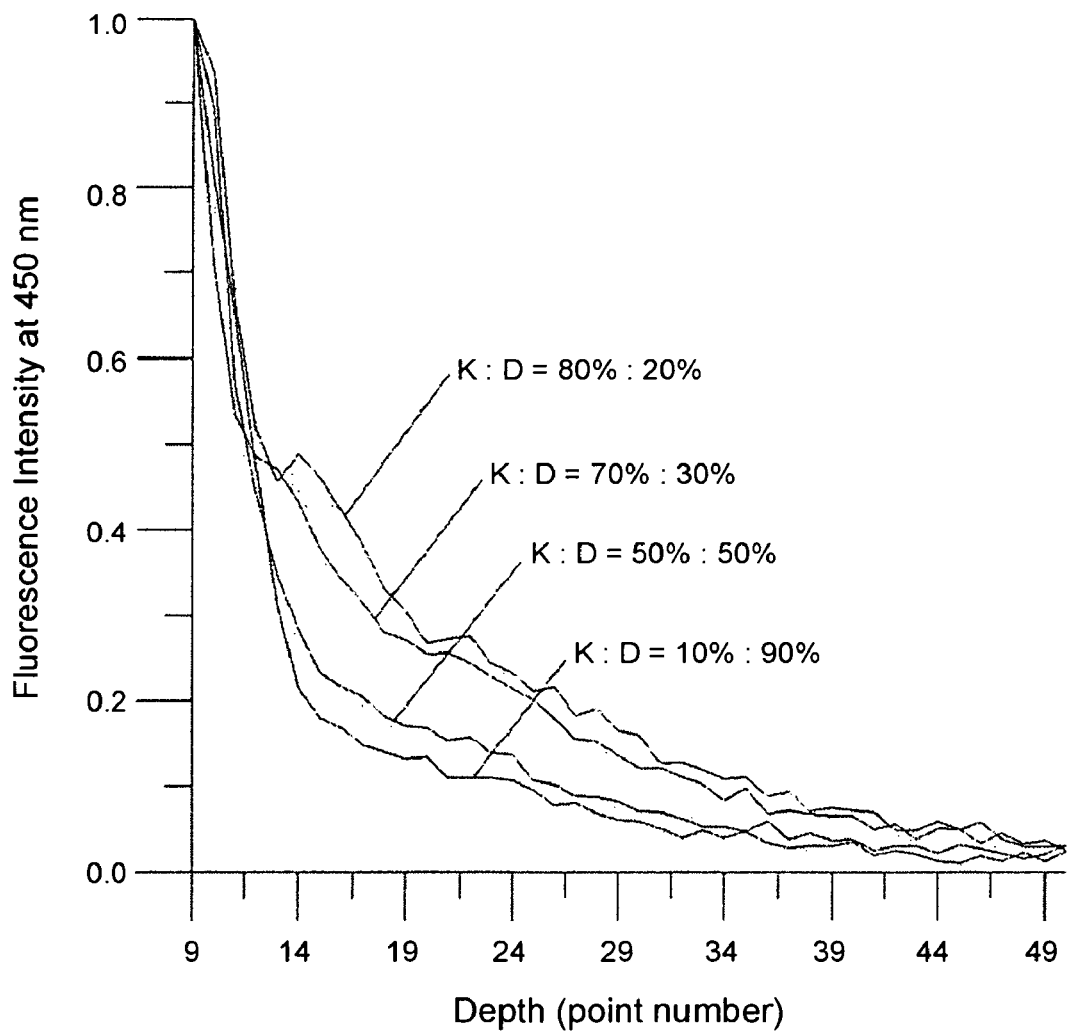
FIG. 7C is a plot of fluorescent intensity vs. depth for selected mixtures of kerosene and diesel oil (diesel oil 10-90%) at an emission wavelength of 450 nm according to the apparatus and method for measuring concentrations of fuel mixtures using depth-resolved laser-induced fluorescence of the present invention.

Referring to FIGS. 7A, 7B, and 7C, there are shown plots of fluorescence intensities emitted at wavelengths 370 nm, 420 nm, and 450 nm, respectively, versus depth for these mixtures. The plots are all normalized at the maximum intensity observed at point no. 9, and they are all shown in sections between point nos. 9 and 50 (corresponding to depths between 1.44 mm and 8.00 mm). It can be seen that the situation here is different from that of Example 1. Here, the intensities at the selected emission wavelengths decrease when the concentration of the diesel fuel increases. This suggests that there is a specific combination of kerosene and diesel fuel concentrations at which a flip-flop in the order of the intensities of the plots takes place.

The plots that have been filtered at 420 nm and 450 nm produce larger intensity variations between the different mixtures, and hence they would provide better calibration curves than those that are filtered at 370 nm. By examining the plots one would immediately predict that such calibration curves would not be linear and that they would have smaller slopes when the diesel oil concentrations exceed 50%.

Figure 7D:
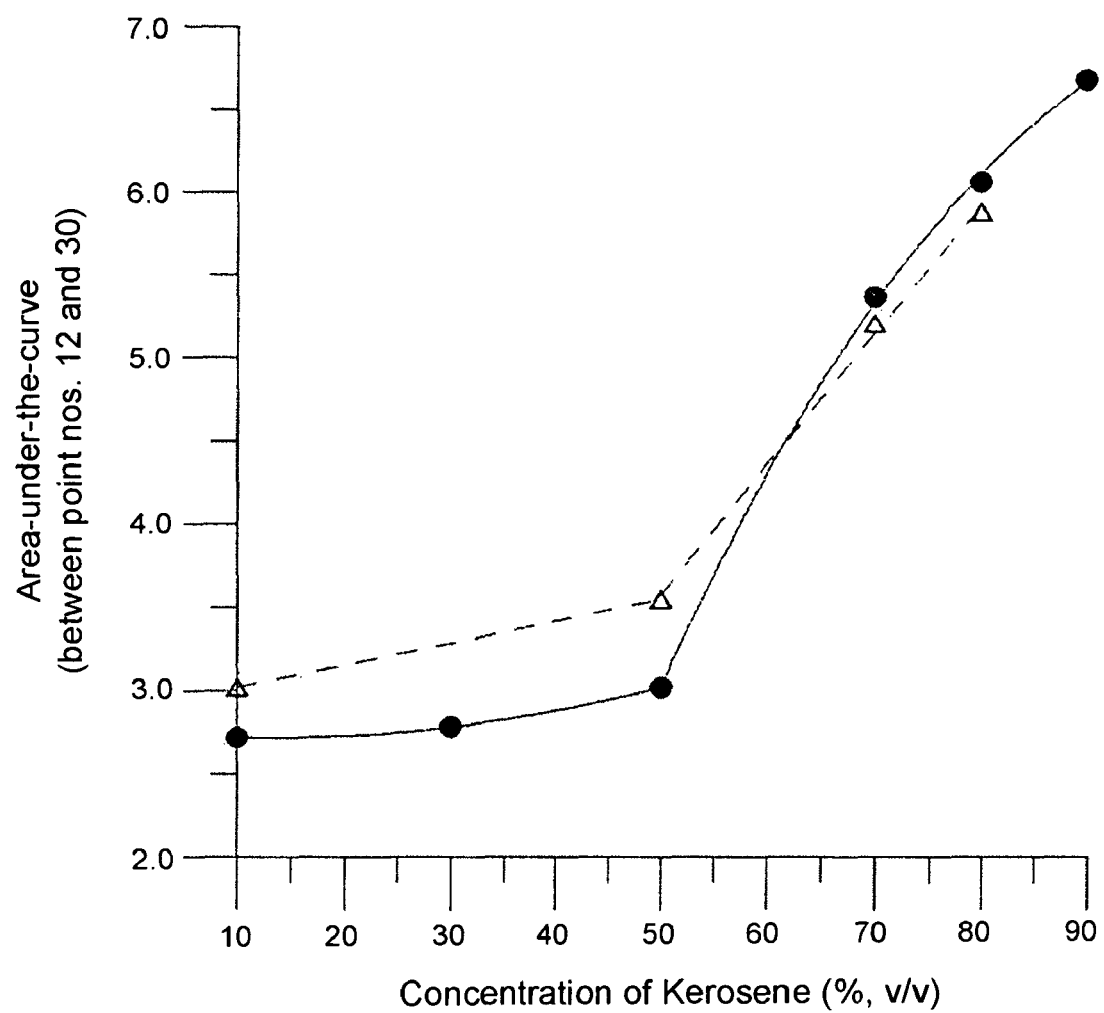
FIG. 7D is a graph showing possible calibration curves for the concentration of kerosene drawn from the intensity vs. depth data of FIGS. 7B (the solid line curve) and 7C (the dashed line curve), respectively, according to the apparatus and method for measuring concentrations of fuel mixtures using depth-resolved laser-induced fluorescence of the present invention.

Referring to FIG. 7D, there is shown two possible calibration curves from which the concentrations could be measured once a particular area-under-the-curve, taken here as the area between point nos. 12 and 30, is measured. The calibration curves utilize the data of FIGS. 7B and 7C, and have been constructed with the peaks normalized to unity at the intensities corresponding to point no. 9. It can be noticed in FIG. 7D that each of the two calibration curves has two distinct regions at both sides of the 50% value, as expected. We should also note that the general behavior of the calibration curves is opposite to those of FIG. 6D. The area-under-the-curve decreases with the increase of kerosene concentration in FIG. 6D, but it increases with the increase of kerosene concentration in FIG. 7D.

Figure 8:
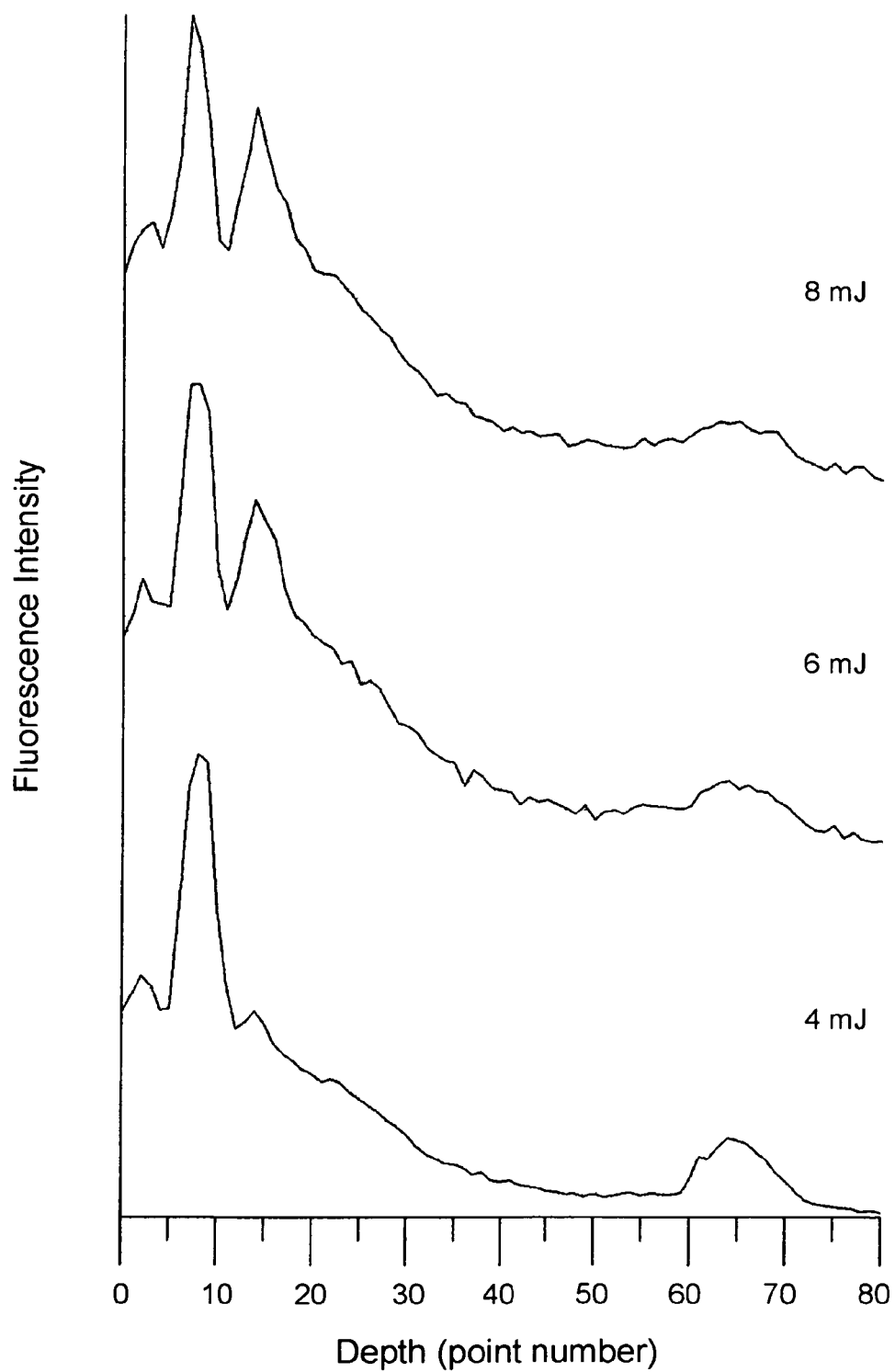
FIG. 8 is a plot of fluorescent intensity vs. depth at an emission wavelength of 420 nm for selected excitation energy levels according to the apparatus and method for measuring concentrations of fuel mixtures using depth-resolved laser-induced fluorescence of the present invention.

The intensity of the laser beam, and also its physical shape, plays an important role in the emission reabsorption processes inside the mixtures. Referring to FIG. 8, there are shown three plots of the intensity of the fluorescence versus depth at an emission wavelength of 420 nm for the same (k %:D %=90:10) mixture. The three plots correspond to laser energies of 4 mJ, 6 mJ, and 8 mJ, and are plotted with the second peaks (at point no. 9) normalized to unity. It is clear that the peak near point no. 15 increases in intensity with laser energy. This stresses the point that the laser energy must be kept constant throughout the measurements. In fact, it can be seen that the peaks near point no. 15, which were prominent in the first example, are much weaker in FIGS. 7B and 7C because the laser pulse energy has been reduced. This also suggests that the flip-flop in the order of the intensities with respect to the diesel fuel depends also on the intensity of the laser beam.

Figure 9:
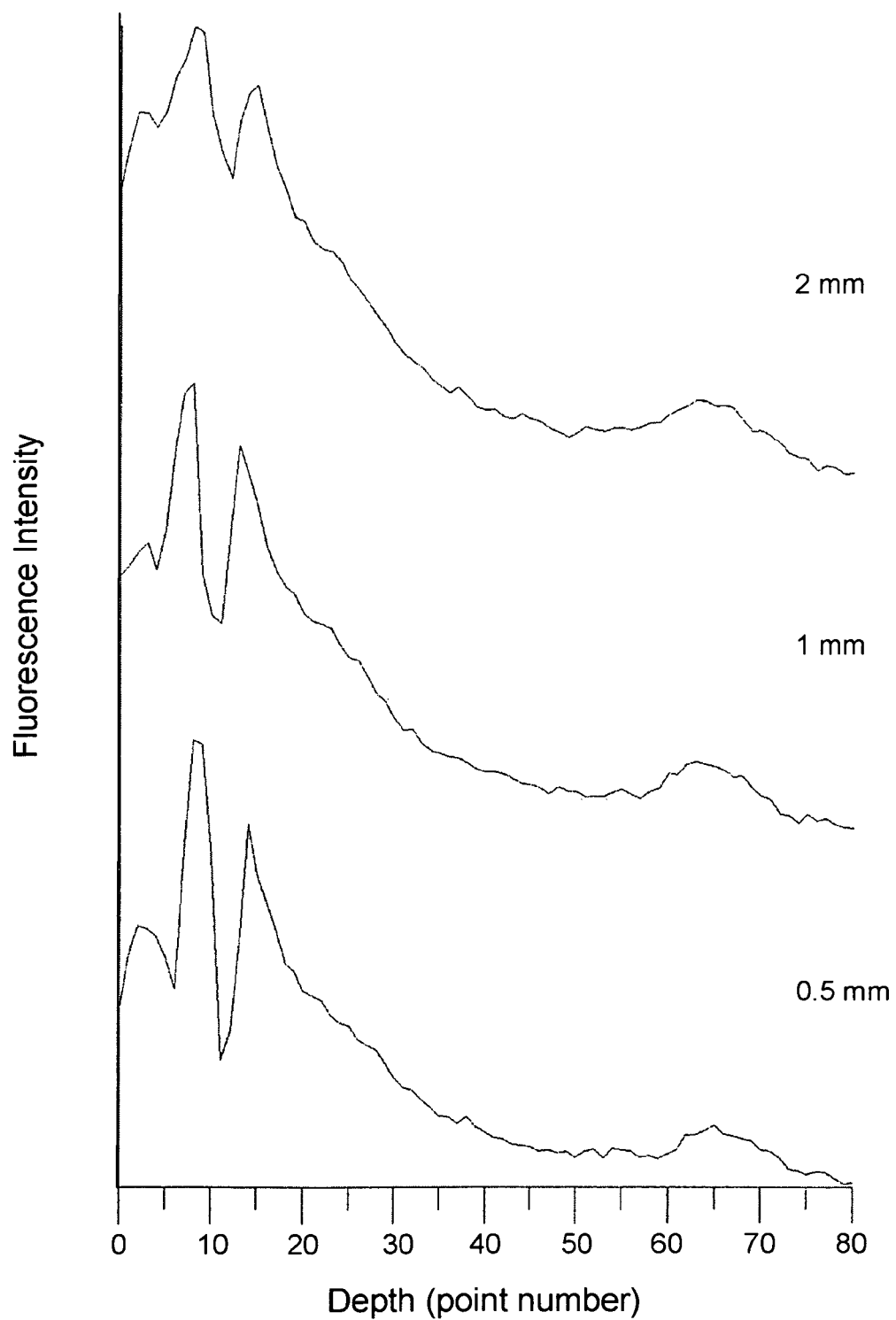
FIG. 9 is a plot of fluorescent intensity vs. depth for a kerosene-diesel oil mixture at an emission wavelength of 420 nm at selected slit sizes according to the apparatus and method for measuring concentrations of fuel mixtures using depth-resolved laser-induced fluorescence of the present invention.

The size of the sample holder slit 24 has also a role to play. It affects the resolution of the peaks in a similar manner that the size of the monochromator's slit does for regular spectra. Referring to FIG. 9, there is shown three plots of the intensity of the fluorescence versus depth at an emission wavelength of 420 nm for the same (k %:D %=90:10) mixture. The three plots correspond to three different sizes for the slit 24, namely, 0.5 mm, 1 mm, and 2 mm. The manner by which the resolution is affected can easily be seen by noticing that, as the slit size decreases, the peak at point no. 15 becomes more separated from the second peak. Plots of better resolution could also be obtained by moving the sample holder in smaller steps.

Example 3

Diesel Fuel Contaminated with Minute Concentrations of Kerosene

Both diesel fuel and kerosene are considered middle distillates of the crude oil. The composition of kerosene includes blends of C9 to C16 hydrocarbons with a boiling range of about 300-550° F., while that of diesel fuel includes blends of C9 to C20 hydrocarbons with boiling range of about 325-675° F. The lighter hydrocarbon blends in the kerosene bring about a narrower fluorescence emission spectrum than that of diesel fuel. Example 1 dealt with a situation in which kerosene, having a narrower spectrum, was contaminated with small amounts of diesel fuel, a blend that has a broader spectrum. In the present example we deal with the reverse case.

Figure 10A:
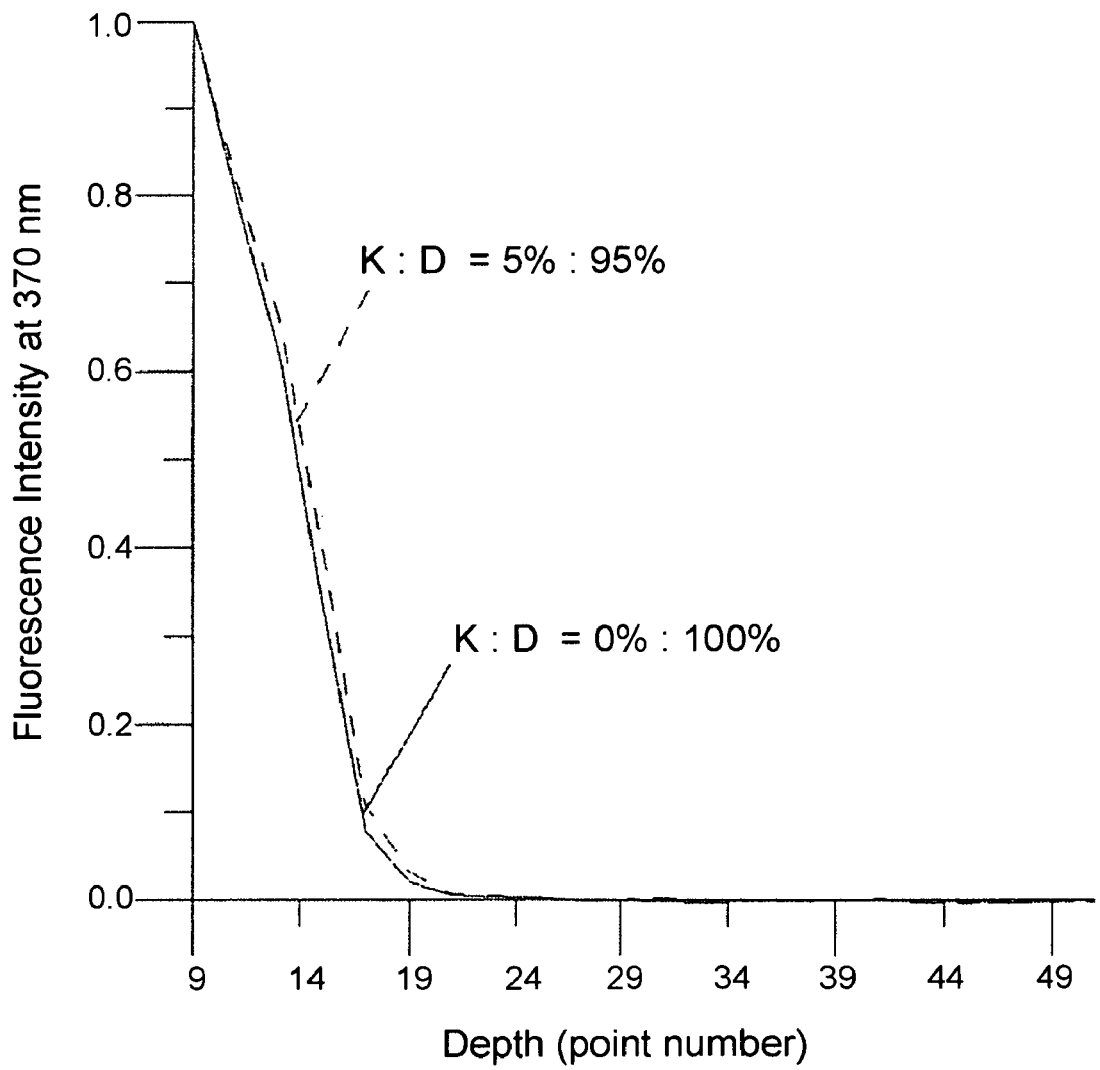
FIG. 10A is a plot of fluorescent intensity vs. depth for selected mixtures of kerosene and diesel oil (kerosene 0-5%) at an emission wavelength of 370 nm according to the apparatus and method for measuring concentrations of fuel mixtures using depth-resolved laser-induced fluorescence of the present invention.
Figure 10B:
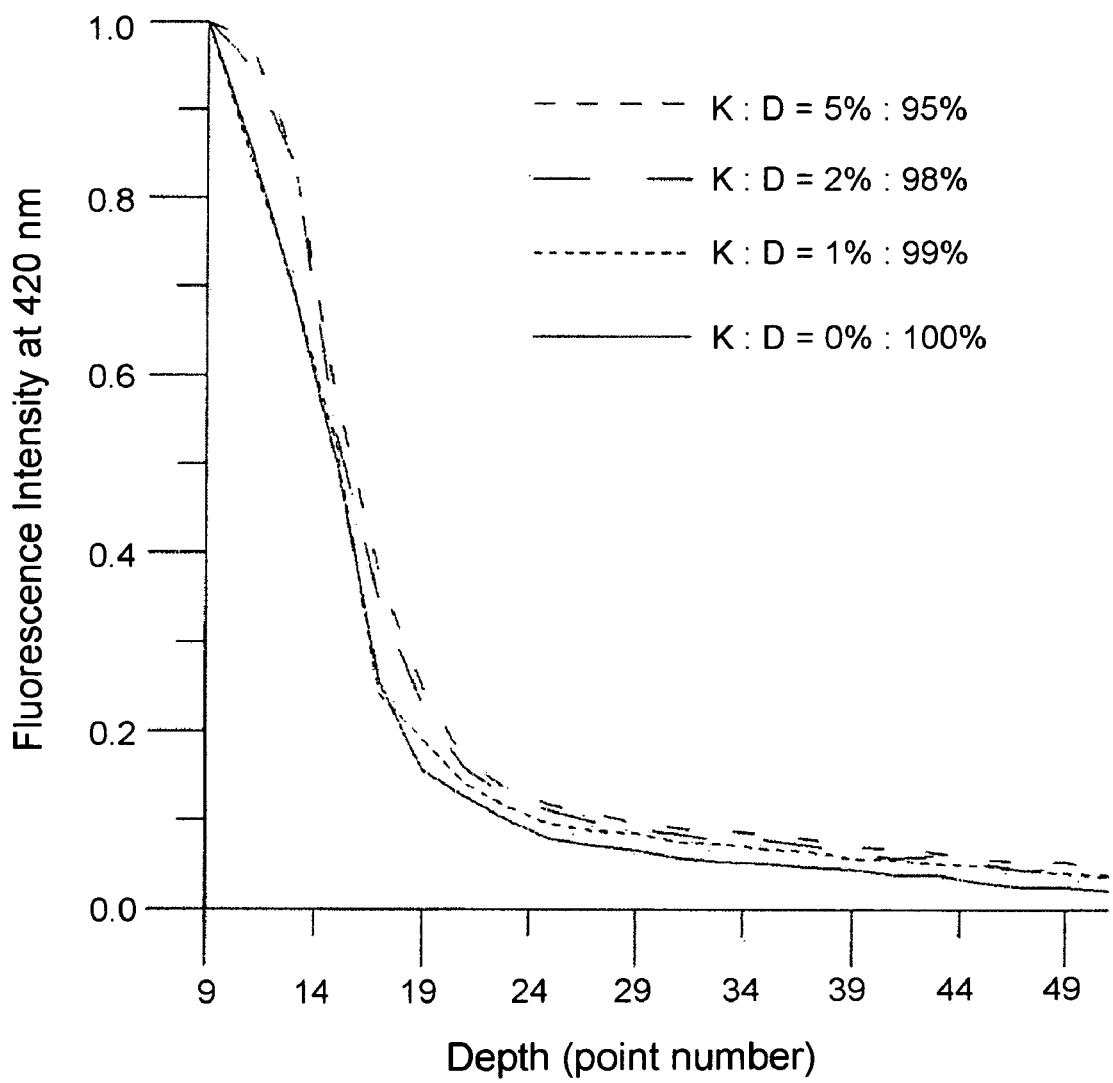
FIG. 10B is a plot of fluorescent intensity vs. depth for selected mixtures of kerosene and diesel oil (kerosene 0-5%) at an emission wavelength of 420 nm according to the apparatus and method for measuring concentrations of fuel mixtures using depth-resolved laser-induced fluorescence of the present invention.
Figure 10C:
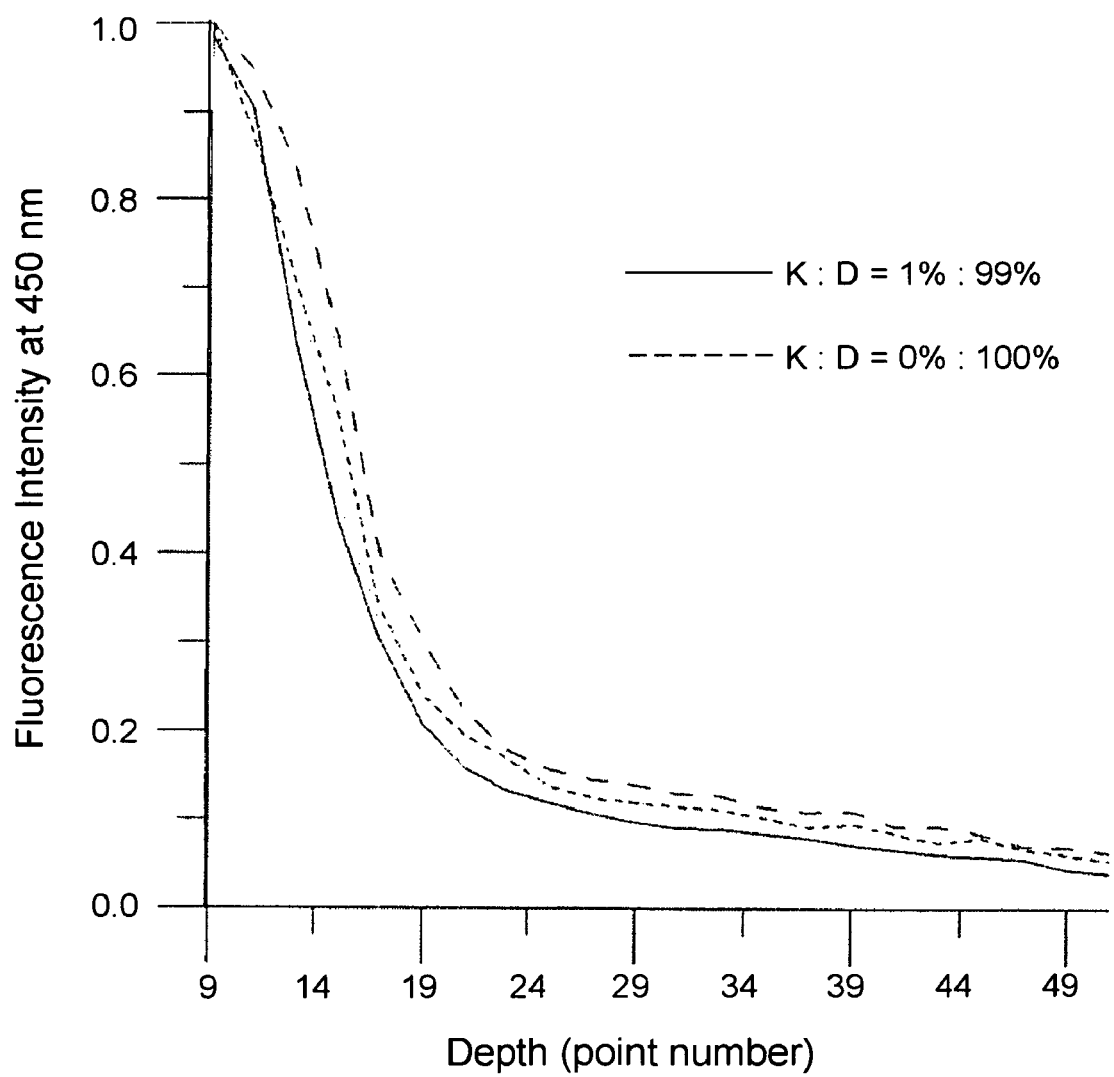
FIG. 10C is a plot of fluorescent intensity vs. depth for selected mixtures of kerosene and diesel oil (kerosene 0-5%) at an emission wavelength of 450 nm according to the apparatus and method for measuring concentrations of fuel mixtures using depth-resolved laser-induced fluorescence of the present invention.

In this example, we consider the kerosene/diesel fuel mixtures of Set 3, which has concentrations of (K %:D %)=(5:95), (3:97), (2:98), (1:99), and (0:100), and we focus only on the second mode of operation. Referring to FIGS. 10A, 10B, and 10C, there are shown plots of fluorescence intensities versus depth at emission wavelengths of 370 nm, 420 nm, and 450 nm, respectively, for these mixtures. The plots are all normalized at the maximum intensity of point no. 9. It can be seen that, as the diesel fuel concentration increases, the overall intensities of the plots continue to decrease systematically throughout the depth of the cuvette, as in Example 2. The only difference is that most of the changes in the intensities with respect to the diesel fuel concentrations occur at a smaller depth than in the cases of Example 2.

The plots of FIGS. 10B and 10C, which are filtered at 420 nm and 450 nm, respectively, show changes that are more significant than those of FIG. 10A, which are filtered at 370 nm. Hence, calibration curves should continue to be constructed at these two wavelength filtrations.

Figure 10D:
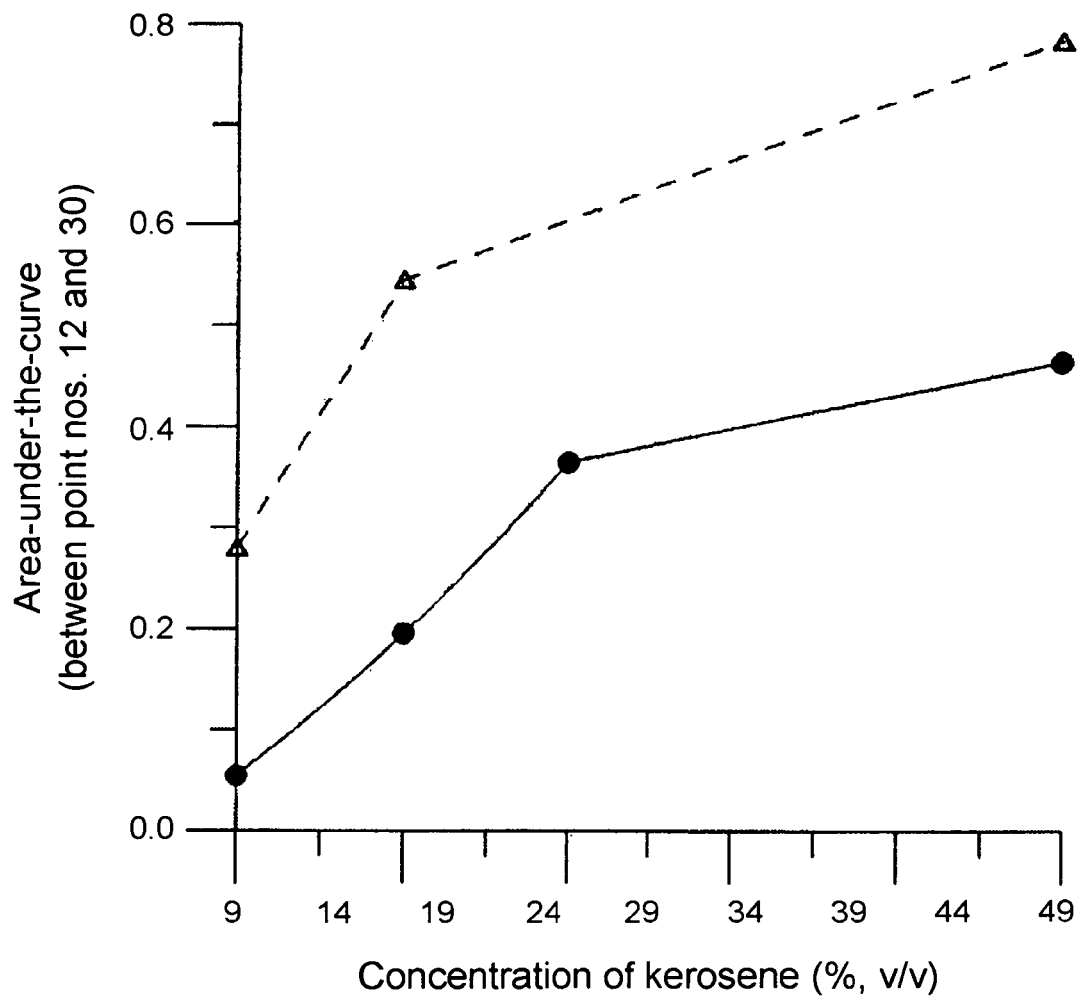
FIG. 10D is a graph showing possible calibration curves for the concentration of kerosene drawn from the intensity vs. depth data of FIGS. 10B (the solid line curve) and 10C (the dashed line curve), respectively, according to the apparatus and method for measuring concentrations of fuel mixtures using depth-resolved laser-induced fluorescence of the present invention.

Referring to FIG. 10D, there is shown two possible calibration curves constructed from FIGS. 10B and 10C by relating the area-under-the-curve between point nos. 12 and 30 to the concentrations of the mixtures. It is obvious that these curves can distinguish between mixtures having diesel oil concentration variations of less than 0.5%.

Example 4

Gasoline Contaminated with Minute Concentrations of Diesel Fuel

This Example considers the case in which pure gasoline is contaminated with minute concentrations of diesel fuel using mixtures of Set 4. Here the two modes of operation will be demonstrated as we did for the kerosene/diesel fuel mixtures in Example 1. However, because the mixtures now include gasoline instead of kerosene, one should expect a different emission-reabsorption scheme, which leads to different shapes of emission spectra and different behavior of intensity-versus-depth plots.

Figure 11A:
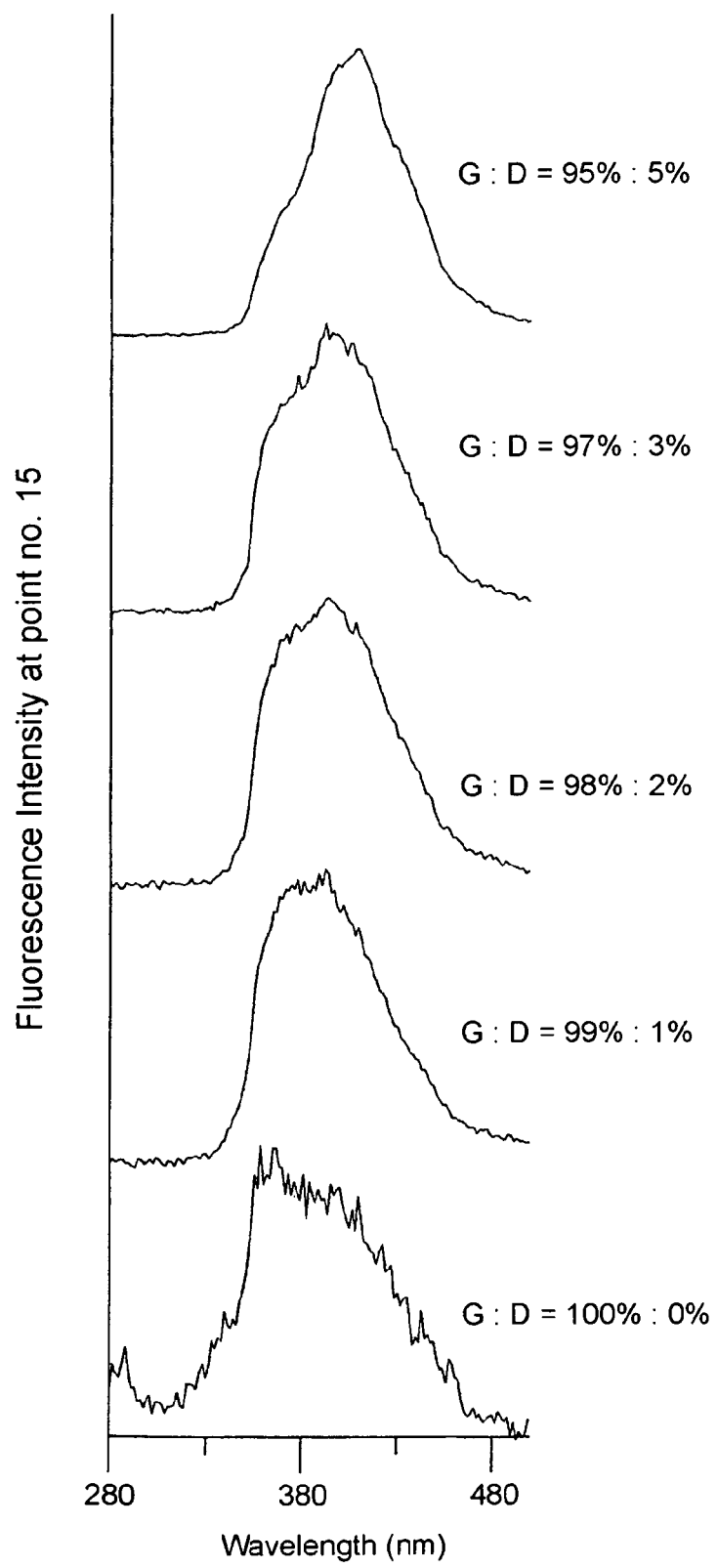
FIG. 11A is the emission spectra of a gasoline and diesel oil mixture (diesel oil 0-5%) at a depth of 15 points (2.40 mm) according to the apparatus and method for measuring concentrations of fuel mixtures using depth-resolved laser-induced fluorescence of the present invention.

Referring to FIG. 11A, there are shown emission spectra for the gasoline/diesel fuel mixtures having concentrations of (G %:D %)=(100:0), (99:1), (98:2), (97:3), and (95:5) and measured at point no. 15. It can be seen that, as in the case of Example 1, as the concentration of diesel fuel increases, the spectra shift more and more toward longer wavelengths. The range of the shift appears to be between 350 nm and 400 nm. Ratios of areas-under-the-curve involving these two wavelengths may then be used to construct a calibration curve for estimating the amount of diesel fuel contaminating the gasoline sample.

Figure 11B:
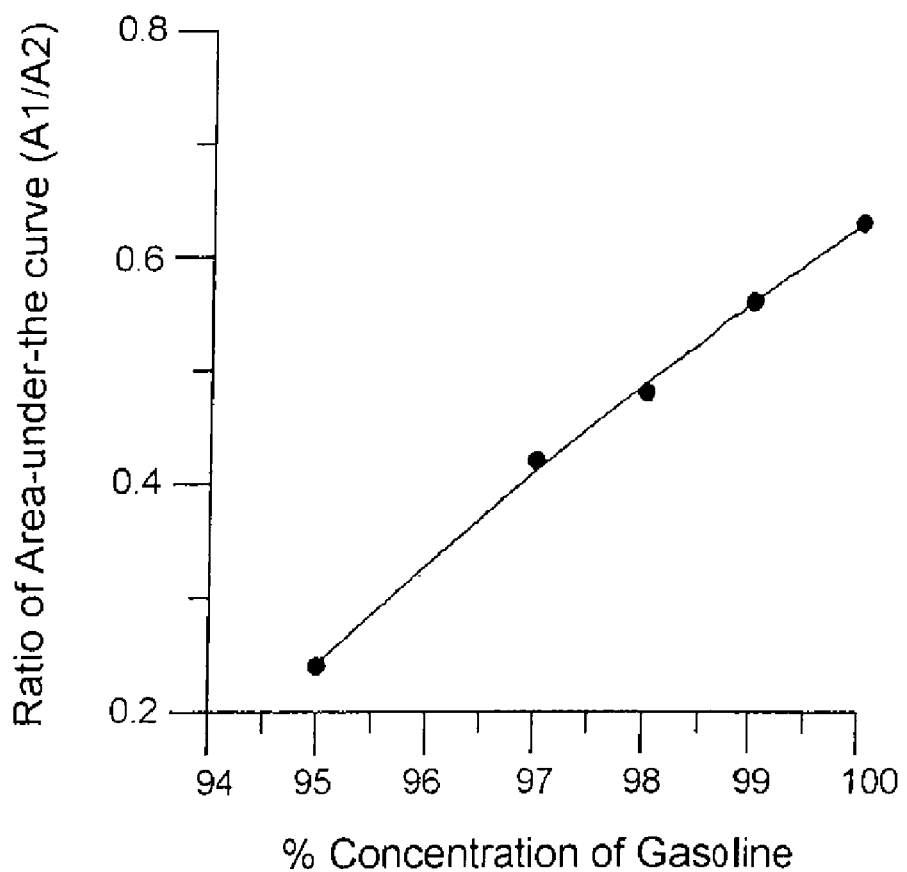
FIG. 11B is a calibration curve for the concentration of gasoline drawn from the data of FIG. 11A according to the apparatus and method for measuring concentrations of fuel mixtures using depth-resolved laser-induced fluorescence of the present invention.

Referring to FIG. 11B, there is shown a possible calibration curve relating the ratios of the areas-under-the-curve $A_1/A_2$ as functions of diesel fuel concentration, where $A_1$ and $A_2$ are the area-under-the-curves from 350 nm to 380 nm and from 380 nm to 450 nm, respectively. It is clear that the curves can distinguish between mixtures having diesel oil concentration variations of less than 0.5%.

Figure 12A:
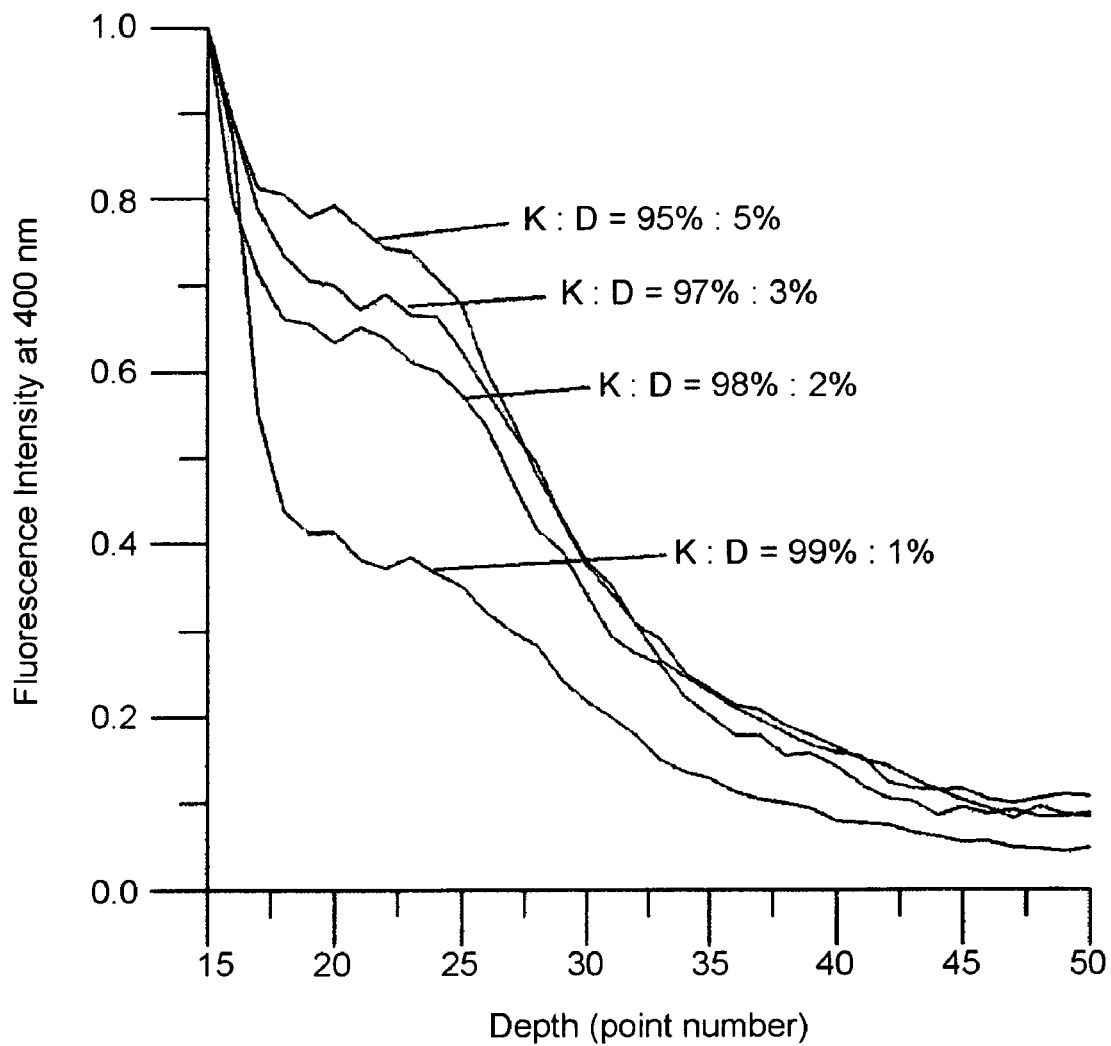
FIG. 12A is a plot of fluorescent intensity vs. depth for selected mixtures of gasoline and diesel oil (diesel oil 1-5%) at an emission wavelength of 400 nm according to the apparatus and method for measuring concentrations of fuel mixtures using depth-resolved laser-induced fluorescence of the present invention.

Now, referring to FIG. 12A, there are shown data collected using the second mode of operation. The data represent intensities of the emitted fluorescence that have been filtered at an emission wavelength of 400 nm as a function of depth. The plots are all normalized at the maximum intensity observed at point no. 15, and they are all shown in sections between point nos. 15 and 50 (corresponding to depths between 2.40 mm and 8.00 mm). It can be seen that, as the concentration of the diesel fuel increases, the intensities also increase. The intensities in these plots can be also utilized to construct a calibration curve for determining the minute changes in the concentrations.

Figure 12B:
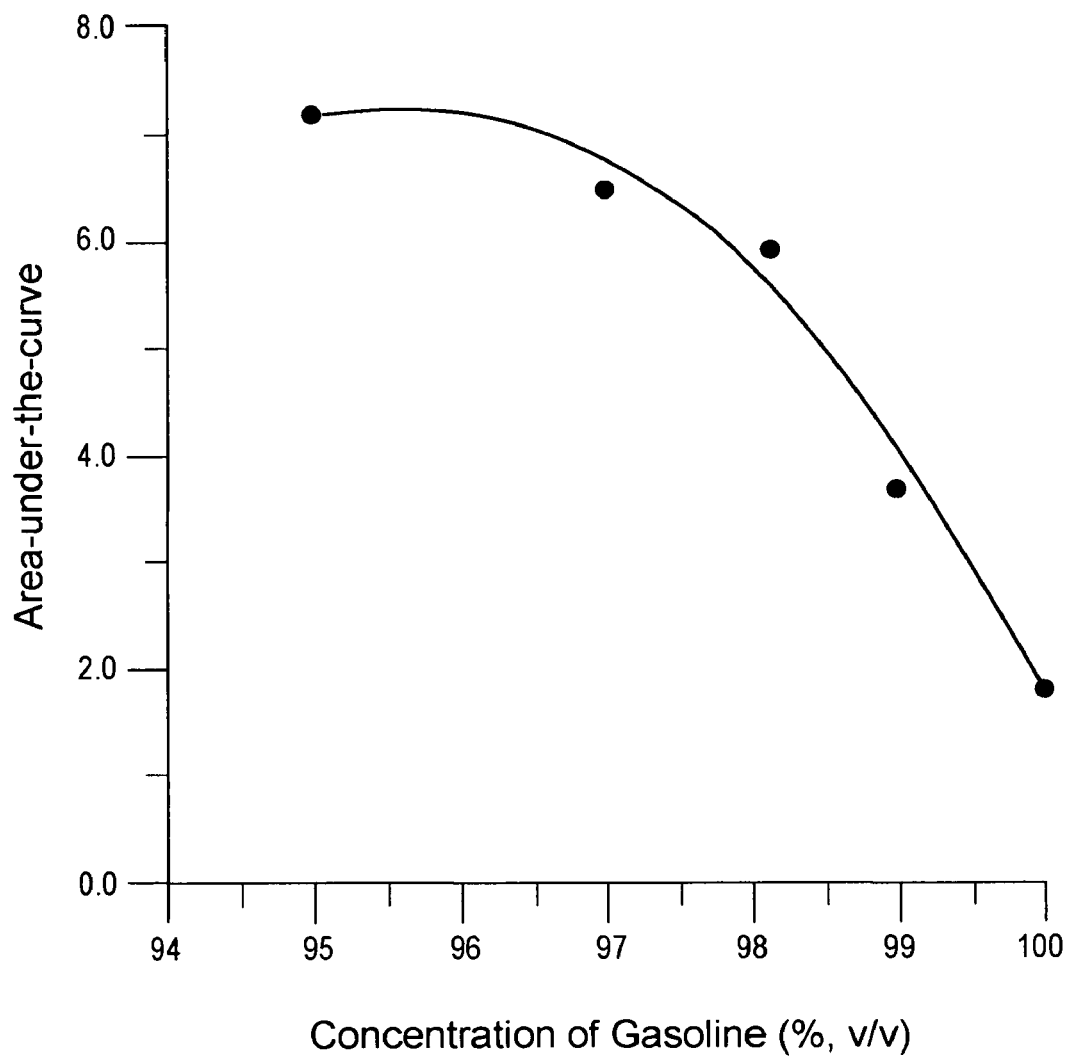
FIG. 12B is a graph showing possible calibration curves for the concentration of gasoline drawn from the intensity vs. depth data of FIG. 12A according to the apparatus and method for measuring concentrations of fuel mixtures using depth-resolved laser-induced fluorescence of the present invention.

Referring to FIG. 12B, there is shown one possible calibration curve. It is constructed by measuring the areas-under-the-curve between point nos. 19 and 29 as functions of concentrations. It is clear that these calibration curves also can distinguish between mixtures having diesel oil concentration variations of less than 0.5%.

Example 5

Gasoline of Octane 95 Contaminated with Gasoline of Octane 91

The final example is concerned with mixtures of two types of gasoline. One type has an octane number of 95 while the other has an octane number of 91. The mixtures are those of Set 5, namely: (Octane (95) %:Octane (91) %)=(100:0), (90: 10), (80:20), and (0:100).

Figure 13:
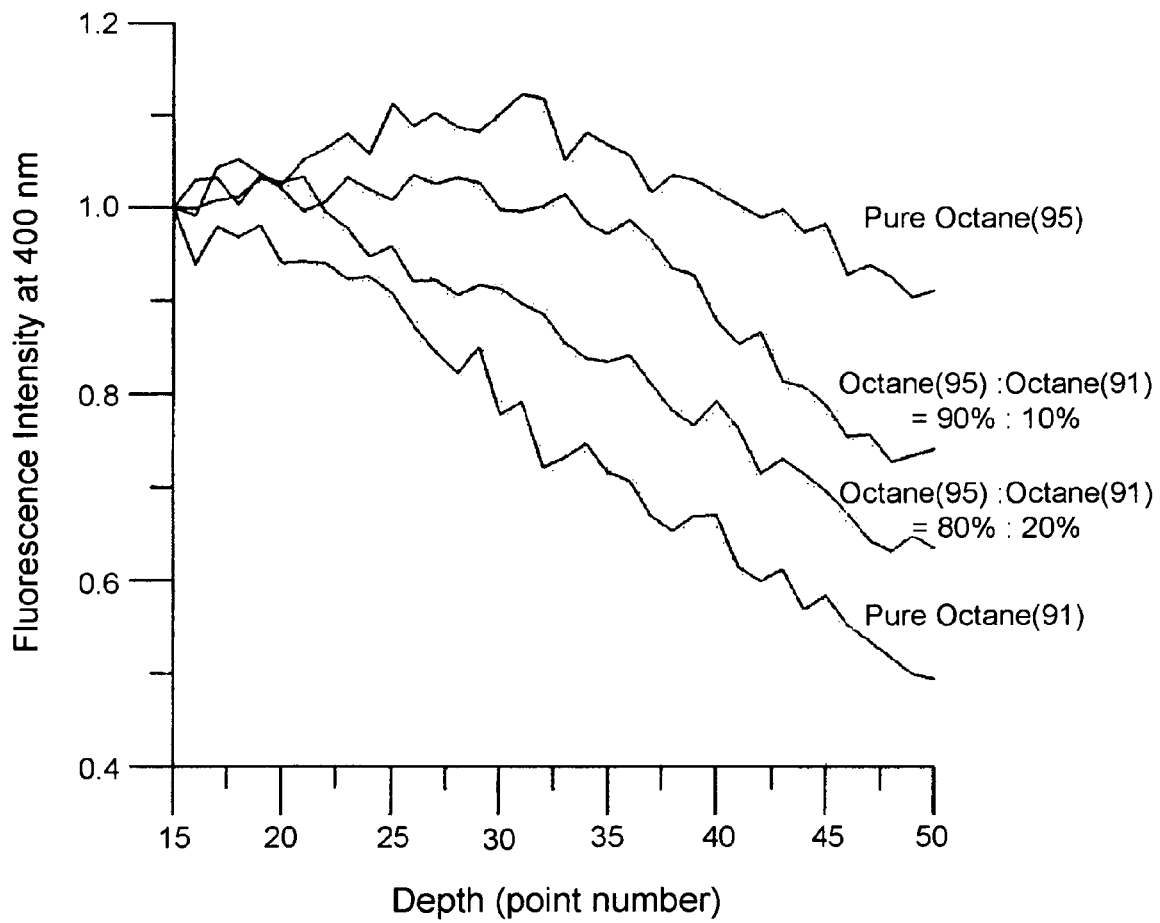
FIG. 13 is a plot of fluorescent intensity vs. depth for selected mixtures of 95-octane gasoline and 91-octane gasoline at an emission wavelength of 400 nm according to the apparatus and method for measuring concentrations of fuel mixtures using depth-resolved laser-induced fluorescence of the present invention.
Figure 14:
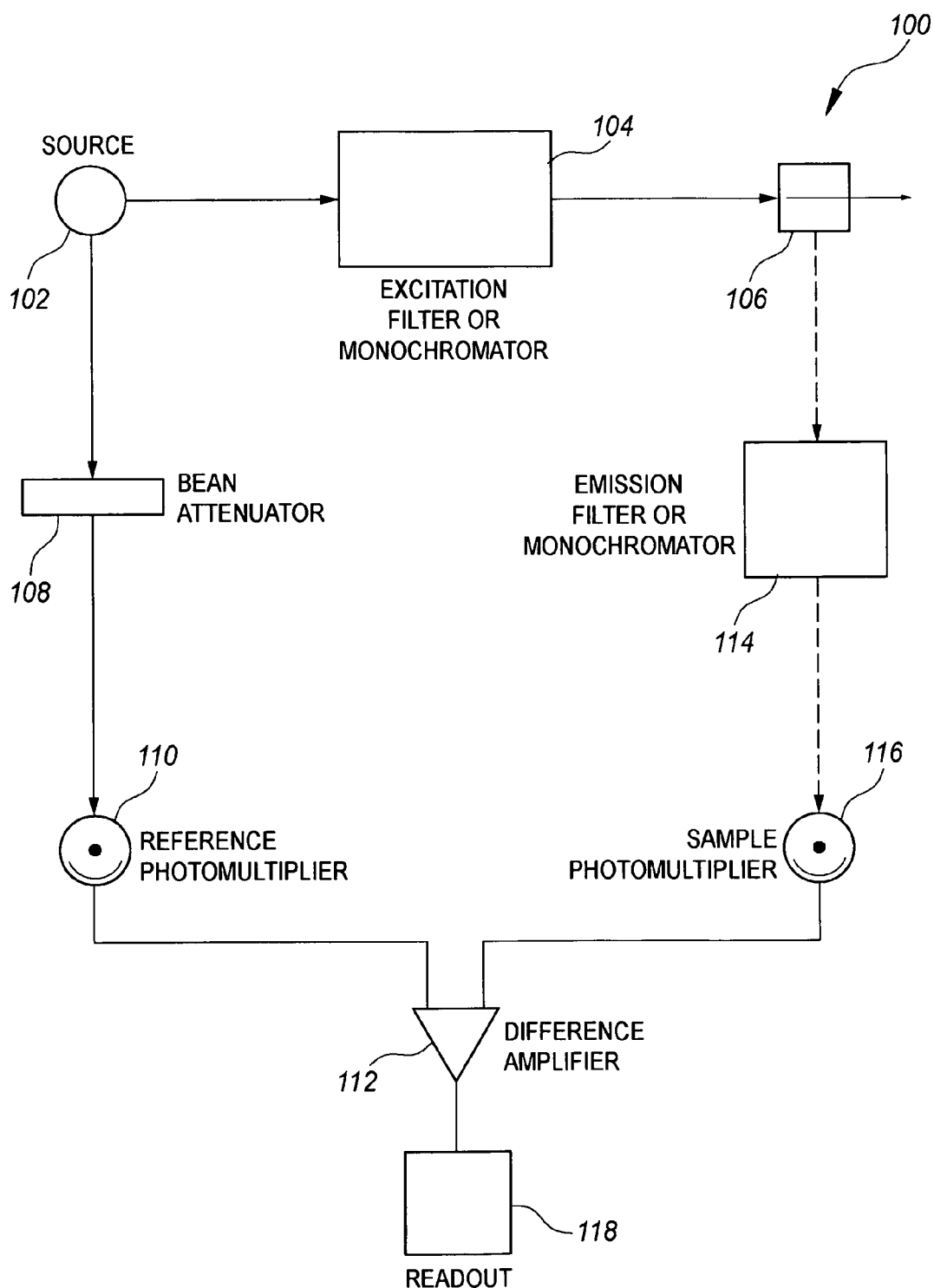
FIG. 14 is a block diagram of a conventional spectrofluorometer according to the prior art.

Referring to FIG. 13, there are shown data collected using the second mode of operation. The data represent intensities of the emitted fluorescence at an emission wavelength of 400 nm as a function of depth. The plots are all normalized at the maximum intensity observed at point no. 15, and they are all shown in sections between point nos. 15 and 50 (corresponding to depths between 2.40 mm and 8.00 mm). It can be seen that the plots can easily distinguish between the pure octane (95) and any mixture containing small contaminations of octane (91). The intensities in such plots can be also utilized to construct calibration curves depending on the range of concentrations.

It is to be understood that the present invention is not limited to the embodiments described above, but encompasses any and all embodiments within the scope of the following claims.

I claim:

1. An apparatus for use in analyzing fluorescent signal intensity of fuel mixtures based on inducing deep-layer fluorescence and using 90° excitation-emission geometry, comprising:
    a support surface;
    a laser operative to generate an excitation light beam of ultraviolet light;
    a sample holder slidably mounted on the support surface in a path of the excitation light beam;
    a sample container for holding a fuel mixture, said sample container being supported by the sample holder and being configured to contain the fuel mixture in the path of the excitation light beam, the sample container being formed from an optically transparent material such that the excitation light beam is directed within the sample container along a first direction parallel to the excitation light beam and onto and through the fuel mixture;
    means for diffracting an emission light beam normal to the excitation light beam from a thin layer of the fuel mixture, said means for diffracting the emission light beam normal to the excitation light beam comprising a screen fixedly disposed adjacent the sample holder and sample container, the screen having a substantially vertical slit defined therein adapted for diffracting fluorescent light emitted from the sample container along a second direction orthogonal to the first direction of the excitation light beam;
    a monochromator disposed in the path of light diffracted by the diffracting means for filtering the diffracted light to an emission wavelength, the monochromator being successively scannable over a spectrum of emission wavelengths;
    a photomultiplier, the monochromator being disposed between the diffracting means and the photomultiplier, the photomultiplier generating a test signal proportional to the intensity of the diffracted light;
    wherein the laser generates a trigger signal proportional to the intensity of the excitation light beam; and
    a signal analyzer for receiving the trigger signal and the test signal and thereafter generating an output signal corresponding to the intensity of the fluorescent light emitted from the sample container.

2. The apparatus for measuring concentrations according to claim 1, further comprising means for moving the sample holder in the path of the excitation light beam so that the light diffracted through the substantially vertical slit in the screen corresponds to fluorescent light emitted from successively deeper portions of the fuel mixture contained within the sample container resulting from deeper penetration of the excitation light beam into the sample container.

3. The apparatus for measuring concentrations according to claim 1, wherein said means for diffracting further comprises:
    a collimating lens positioned between the screen and said monochromator; and
    a focusing lens disposed between the collimating lens and said monochromator.

* * * * *